(12) United States Patent
Kim et al.

(10) Patent No.: US 11,038,119 B2
(45) Date of Patent: Jun. 15, 2021

(54) ORGANIC COMPOUND, ORGANIC OPTOELECTRONIC DEVICE AND DISPLAY APPARATUS

(71) Applicant: SAMSUNG SDI CO., LTD., Yongin-si (KR)

(72) Inventors: Jun Seok Kim, Suwon-si (KR); Changwoo Kim, Suwon-si (KR); Byungku Kim, Suwon-si (KR); Byoungkwan Lee, Suwon-si (KR); Kipo Jang, Suwon-si (KR); Ho Kuk Jung, Suwon-si (KR); Eun Sun Yu, Suwon-si (KR); Sung-Hyun Jung, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 351 days.

(21) Appl. No.: 16/072,297

(22) PCT Filed: Sep. 21, 2016

(86) PCT No.: PCT/KR2016/010522
§ 371 (c)(1),
(2) Date: Jul. 24, 2018

(87) PCT Pub. No.: WO2017/135546
PCT Pub. Date: Aug. 10, 2017

(65) Prior Publication Data
US 2019/0013482 A1 Jan. 10, 2019

(30) Foreign Application Priority Data
Feb. 3, 2016 (KR) .................. 10-2016-0013684

(51) Int. Cl.
*H01L 51/50* (2006.01)
*H01L 51/00* (2006.01)
(Continued)

(52) U.S. Cl.
CPC ........ *H01L 51/0072* (2013.01); *C07D 487/04* (2013.01); *C09K 11/06* (2013.01); *H01L 51/0067* (2013.01); *H01L 51/5012* (2013.01)

(58) Field of Classification Search
None
See application file for complete search history.

(56) References Cited

U.S. PATENT DOCUMENTS

| 8,637,857 B2 | 1/2014 | Langer et al. |
| 8,795,848 B2 | 8/2014 | Kai et al. |
| 2017/0047527 A1* | 2/2017 | Lee ..................... H01L 51/0065 |

FOREIGN PATENT DOCUMENTS

| CN | 101161765 A | 4/2008 |
| CN | 103958642 A | 7/2014 |

(Continued)

OTHER PUBLICATIONS

Chinese Office Action dated Apr. 29, 2020, and the Chinese Search Report dated Apr. 20, 2020, of the corresponding Chinese Patent Application No. 201680080086.0.

*Primary Examiner* — Gregory D Clark
(74) *Attorney, Agent, or Firm* — Lee IP Law, PC

(57) ABSTRACT

The present invention relates to an organic compound in which moieties represented by chemical formulae 1 to 3 are bonded in order, an organic optoelectronic device comprising the organic compound and a display apparatus.

15 Claims, 1 Drawing Sheet

(51) Int. Cl.
    *C07D 487/04*     (2006.01)
    *C09K 11/06*     (2006.01)

(56) References Cited

FOREIGN PATENT DOCUMENTS

| | | |
|---|---|---|
| CN | 104011893 A | 8/2014 |
| JP | 4870245 B2 | 2/2012 |
| JP | 5238025 B2 | 7/2013 |
| JP | 5646733 B2 | 12/2014 |
| JP | 5723794 B2 | 5/2015 |
| KR | 10-2011-0048838 A | 5/2011 |
| KR | 10-2012-0013278 A | 2/2012 |
| KR | 10-2012-0052879 A | 5/2012 |
| KR | 10-2013-0073537 A | 7/2013 |
| KR | 10-2013-0084093 A | 7/2013 |
| KR | 10-2013-0112342 A | 10/2013 |
| KR | 10-1324788 B1 | 10/2013 |
| KR | 10-2013-0127563 A | 11/2013 |
| KR | 10-2013-0132226 A | 12/2013 |
| KR | 10-1423066 B1 | 7/2014 |
| KR | 10-2014-0113672 A | 9/2014 |
| KR | 10-1447959 B1 | 9/2014 |
| KR | 10-2015-0124902 A | 11/2015 |
| KR | 10-2016-0011582 A | 2/2016 |
| WO | WO 2012/114928 A1 | 8/2012 |
| WO | WO 2013/088973 A1 | 6/2013 |
| WO | WO 2015-167259 A1 | 11/2015 |
| WO | WO 2016-013875 A1 | 1/2016 |

* cited by examiner

[Fig. 1]
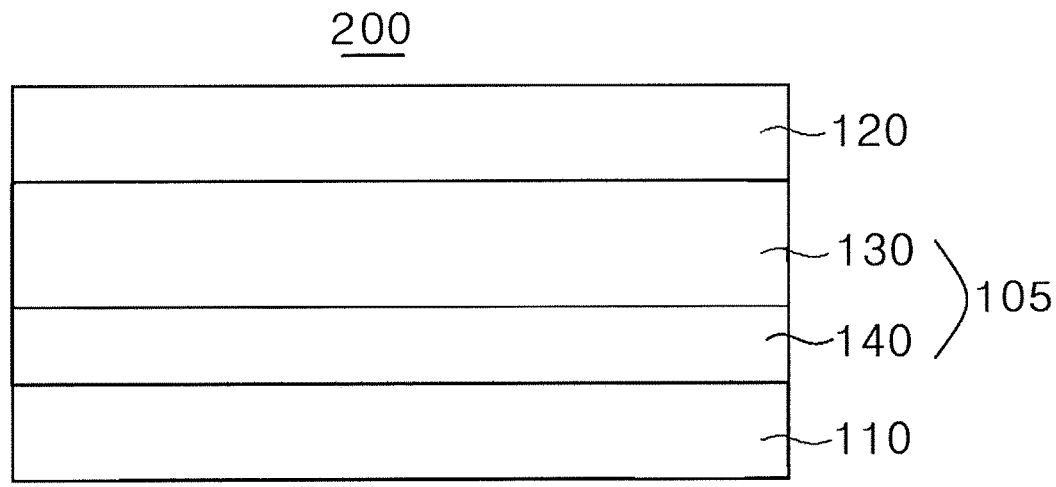
[Fig. 2]
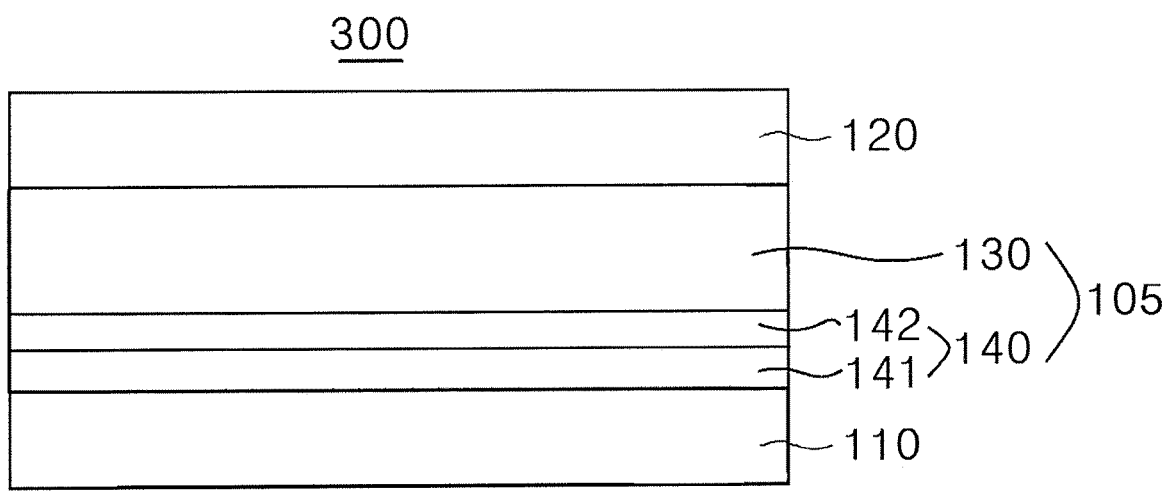

ORGANIC COMPOUND, ORGANIC OPTOELECTRONIC DEVICE AND DISPLAY APPARATUS

CROSS-REFERENCE TO THE RELATED APPLICATION

This is the U.S. national phase application based on PCT Application No. PCT/KR2016/010522, filed Sep. 21, 2016, which is based on Korean Patent Application No. 10-2016-0013684, filed Feb. 3, 2016, the entire contents of all of which are hereby incorporated by reference.

TECHNICAL FIELD

An organic compound, an organic optoelectronic device, and a display apparatus are disclosed.

BACKGROUND ART

An organic optoelectronic device is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides an organic compound being capable of realizing an organic optoelectronic diode having high efficiency and long life-span.

Another embodiment provides an organic optoelectronic device comprising the organic compound.

Yet another embodiment provides a display apparatus including the organic optoelectronic device.

Technical Solution

According to an embodiment, an organic compound in which moieties represented by chemical formulae 1 to 3 are bonded in order is provided.

[Chemical Formula 1]

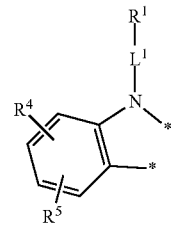

[Chemical Formula 2]

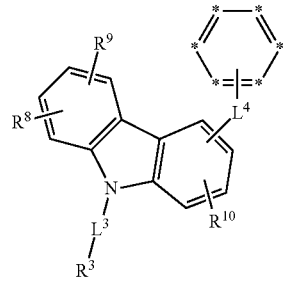

[Chemical Formula 3]

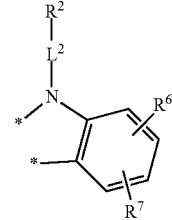

In Chemical Formulae 1 to 3, adjacent two *'s of Chemical Formula 2 are bonded with two *'s of Chemical Formula 1, other adjacent two *'s of Chemical Formula 2 are bonded with two *'s of Chemical Formula 3,

* not being bonded with Chemical Formula 1 or 3 is C or $CR^{11}$, $L^1$ to $L^3$ are independently a single bond or a substituted or unsubstituted C6 to C20 arylene group, $L^4$ is a substituted or unsubstituted C6 to C20 arylene group, $R^1$ to $R^{10}$ are independently hydrogen, deuterium, a substituted or unsubstituted C1 to C20 alkyl group, a substituted or unsubstituted C6 to C30 aryl group, a substituted or unsubstituted amino group, or a combination thereof, and $R^{11}$ is hydrogen, deuterium, a C1 to C20 alkyl group, a C6 to C12 aryl group, a substituted or unsubstituted amino group, or a combination thereof.

The moieties represented by Chemical Formulae 1 to 3 do not have the following structure as follows.

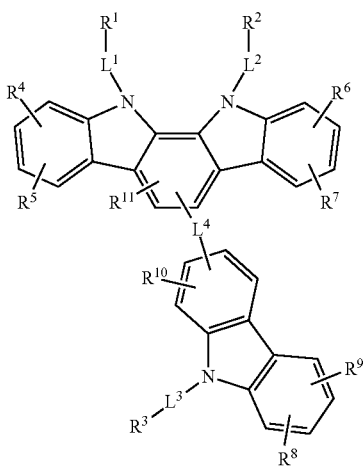

wherein, $L^1$ to $L^4$, and $R^1$ to $R^{11}$ are the same as defined above.

According to another embodiment, an organic optoelectronic device includes an anode and a cathode facing each other and at least one organic layer disposed between the anode and the cathode, wherein the organic layer includes the organic compound.

According to another embodiment, a display apparatus including the organic optoelectronic device is provided.

Advantageous Effects

An organic optoelectronic device having high efficiency and a long life-span may be realized.

DESCRIPTION OF THE DRAWINGS

FIG. 1 is a cross-sectional view showing an organic light emitting diode according to an embodiment, and FIG. 2 is a cross-sectional view showing an organic light emitting diode according to another embodiment.

BEST MODE

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxy group, an amino group, a substituted or unsubstituted C1 to C30 amine group, a nitro group, a C1 to C40 silyl group, a C1 to C30 alkyl group, a C1 to C10 alkylsilyl group, a C6 to C30 aryl group, a C2 to C30 heterocyclic group, a C1 to C20 alkoxy group, a C1 to C10 trifluoroalkyl group such as a trifluoromethyl group, or a cyano group.

In addition, two adjacent substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C6 to C30 aryl group, C3 to C30 heterocyclic group, C1 to C20 alkoxy group, C1 to C10 trifluoroalkyl group such as a trifluoromethyl group, or cyano group may be fused to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one heteroatom and remaining carbons in one functional group. The heteroatom may be selected from N, O, S, P, and Si.

In the present specification, "aryl group" refers to a group including at least one carbocyclic aromatic moiety, and includes carbocyclic aromatic moieties linked by a single bond and carbocyclic aromatic moieties fused directly or indirectly to provide a non-aromatic fused ring. The aryl group may include a monocyclic, polycyclic or fused polycyclic (i.e., rings sharing adjacent pairs of carbon atoms) functional group.

In the present specification "heterocyclic group" refers to a cyclic compound such as an aryl group, a cycloalkyl group, a fused ring thereof, or a combination thereof including at least one selected from N, O, S, P, and Si and remaining carbon. When the heterocyclic group is a fused ring, the entire ring or each ring of the heterocyclic group may include one or more heteroatoms.

More specifically, the substituted or unsubstituted aryl group and/or the substituted or unsubstituted hetero cyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted terphenyl group, a substituted or unsubstituted quaterphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, a combination thereof, or a combined fused ring of the foregoing groups, but are not limited thereto.

In the present specification, hole characteristics refer to an ability to donate an electron to form a hole when an electric field is applied, and that a hole formed in the anode may be easily injected into a light emitting layer, and a hole formed in a light emitting layer may be easily transported into an anode and transported in the light emitting layer due to conductive characteristics according to a highest occupied molecular orbital (HOMO) level.

In addition, electron characteristics refer to an ability to accept an electron when an electric field is applied, and that an electron formed in a cathode may be easily injected into a light emitting layer, and an electron formed in a light emitting layer may be easily transported into a cathode and transported in the light emitting layer due to conductive characteristics according to a lowest unoccupied molecular orbital (LUMO) level.

Hereinafter, an organic compound according to an embodiment is described.

An organic compound according to an embodiment has a structure in which moieties represented by chemical formulae 1 to 3 are bonded in order.

[Chemical Formula 1]

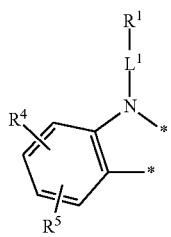

[Chemical Formula 2]

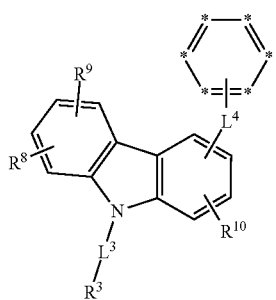

[Chemical Formula 3]

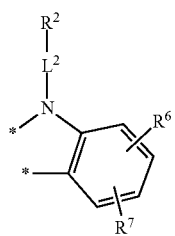

In Chemical Formulae 1 to 3,
adjacent two *'s of Chemical Formula 2 are bonded with two *'s of Chemical Formula 1,
other adjacent two *'s of Chemical Formula 2 are bonded with two *'s of Chemical Formula 3,
* not being bonded with Chemical Formula 1 or 3 is C or $CR^{11}$,
$L^1$ to $L^3$ are independently a single bond or a substituted or unsubstituted C6 to C20 arylene group,
$L^4$ is a substituted or unsubstituted C6 to C20 arylene group,
$R^1$ to $R^{10}$ are independently hydrogen, deuterium, a substituted or unsubstituted C1 to C20 alkyl group, a substituted or unsubstituted C6 to C30 aryl group, a substituted or unsubstituted amino group, or a combination thereof, and $R^{11}$ is hydrogen, deuterium, a C1 to C20 alkyl group, a C6 to C12 aryl group, a substituted or unsubstituted amino group, or a combination thereof, provided, that the moieties represented by Chemical Formulae 1 to 3 do not have the following structure as follows.

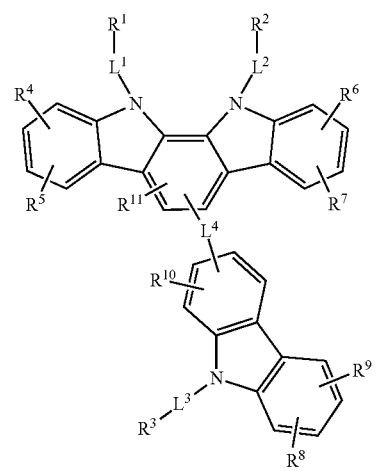

wherein,
$L^1$ to $L^4$, and $R^1$ to $R^{11}$ are the same as defined above.

The structure in which moieties represented by Chemical Formulae 1 to 3 are bonded in order forms an indolocarbazole moiety substituted with a carbazole group.

The organic compound has improved hole transport properties by linking a certain position of the indolocarbazole moiety with C (carbon) of the carbazole group having hole characteristics through an arylene linker. In addition, the organic compound has a structure having high electronic stability compared with the excluded compound and thereby a device including the organic compound has a low driving voltage and simultaneously improves life-span and efficiency characteristics.

For example, $L^4$ that links the indolocarbazole moiety with the carbazole group may be a substituted or unsubstituted phenylene group, a substituted or unsubstituted naphthylene group, a substituted or unsubstituted biphenylene group, a substituted or unsubstituted terphenylene group, or a combination thereof.

For example, $L^4$ may be a substituted or unsubstituted phenylene group.

For example $L^4$ may be a substituted or unsubstituted m-phenylene group, a substituted or unsubstituted p-phenylene group, or a combination thereof.

For example, $L^1$ to $L^3$ may independently be a single bond, a substituted or unsubstituted phenylene group, a substituted or unsubstituted naphthylene group, a substituted or unsubstituted biphenylene group, a substituted or unsubstituted terphenylene group, or a combination thereof.

For example, $R^1$ to $R^3$ may independently be a substituted or unsubstituted C6 to C30 aryl group.

For example, $R^1$ to $R^3$ may independently be a substituted or unsubstituted phenyl group, a substituted or unsubstituted biphenyl group or a substituted or unsubstituted terphenyl group.

For example, at least one of $R^1$ to $R^3$ may be a substituted or unsubstituted phenyl group.

For example, at least two of $R^1$ to $R^3$ may be a substituted or unsubstituted phenyl group.

For example, $R^4$ to $R^{11}$ may independently be hydrogen or deuterium.

The organic compound may be for example represented by one of Chemical Formulae 4 to 7.

[Chemical Formula 4]

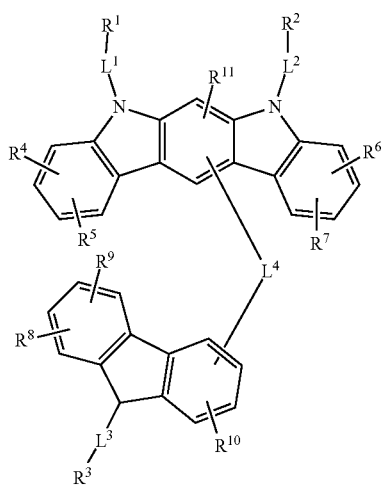

[Chemical Formula 5]

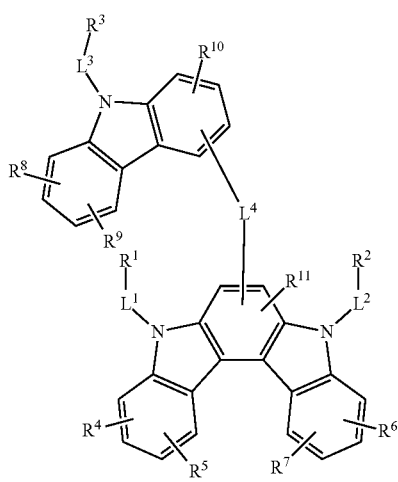

[Chemical Formula 6]

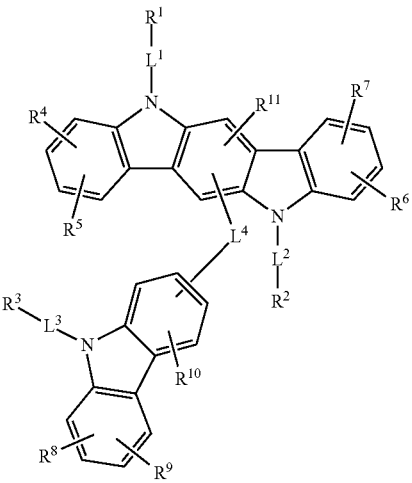

[Chemical Formula 7]

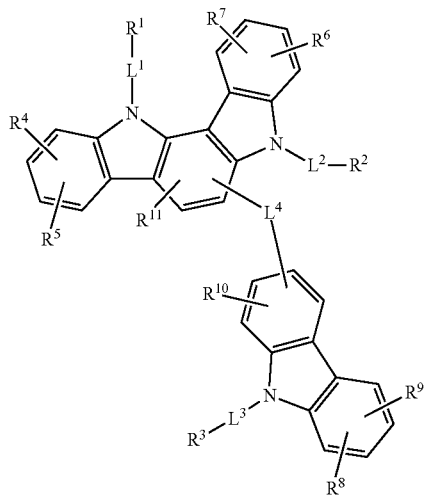

wherein, in Chemical Formulae 4 to 7, $L^1$ to $L^4$ and $R^1$ to $R^{11}$ are the same as described above.

For example, $L^4$ of Chemical Formulae 4 to 7 may be a substituted or unsubstituted phenylene group, a substituted or unsubstituted naphthylene group, a substituted or unsubstituted biphenylene group, a substituted or unsubstituted terphenylene group, or a combination thereof.

For example, $L^4$ of Chemical Formulae 4 to 7 may be a substituted or unsubstituted phenylene group.

For example, $L^4$ of Chemical Formulae 4 to 7 may be a substituted or unsubstituted m-phenylene group, a substituted or unsubstituted p-phenylene group, or a combination thereof.

For example, $L^1$ to $L^3$ of Chemical Formulae 4 to 7 may independently be a single bond, a substituted or unsubstituted phenylene group, a substituted or unsubstituted naphthylene group, a substituted or unsubstituted biphenylene group, a substituted or unsubstituted terphenylene group, or a combination thereof.

For example, $L^1$ to $L^3$ of Chemical Formulae 4 to 7 may independently be a substituted or unsubstituted C6 to C30 aryl group.

For example, $L^1$ to $L^3$ of Chemical Formulae 4 to 7 may independently be a substituted or unsubstituted phenyl group, a substituted or unsubstituted biphenyl group, or a substituted or unsubstituted terphenyl group.

For example, at least one of $L^1$ to $L^3$ of Chemical Formulae 4 to 7 may independently be a substituted or unsubstituted phenyl group.

For example, at least two of $L^1$ to $L^3$ of Chemical Formulae 4 to 7 may independently be a substituted or unsubstituted phenyl group.

For example, $R^4$ to $R^{11}$ of Chemical Formulae 4 to 7 may be hydrogen or deuterium.

The organic compound represented by Chemical Formula 4 may for example be represented by one of Chemical Formulae 4a to 4d according to bonding positions.

[Chemical Formula 4a]

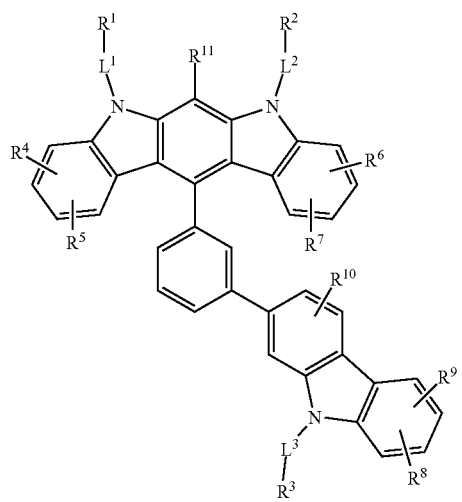

[Chemical Formula 4b]

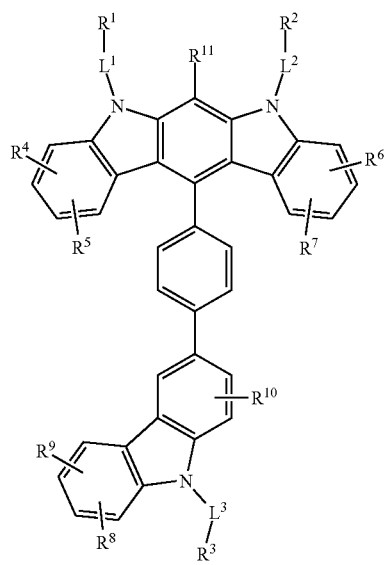

[Chemical Formula 4c]

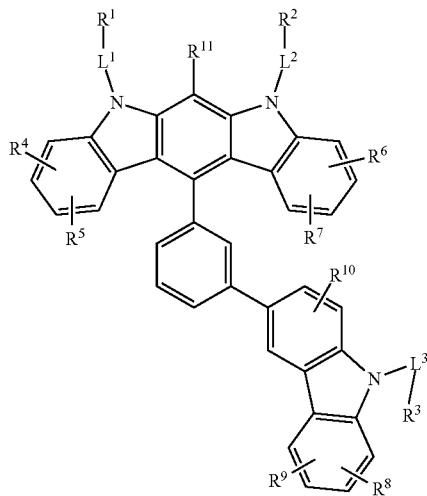

[Chemical Formula 4d]

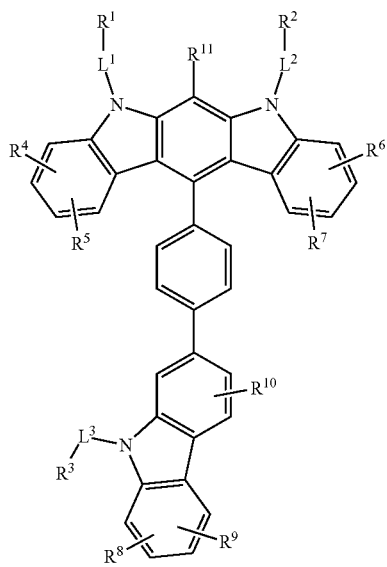

In Chemical Formulae 4a to 4d, $L^1$ to $L^3$ and $R^1$ to $R^{11}$ are the same as described above.

The organic compound represented by Chemical Formula 5 may for example be represented by one of Chemical Formulae 5a to 5d according to bonding positions.

[Chemical Formula 5a]
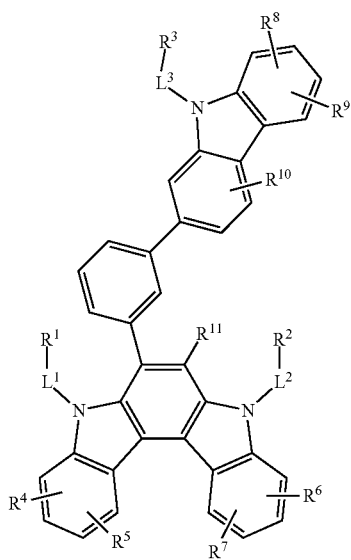
[Chemical Formula 5c]
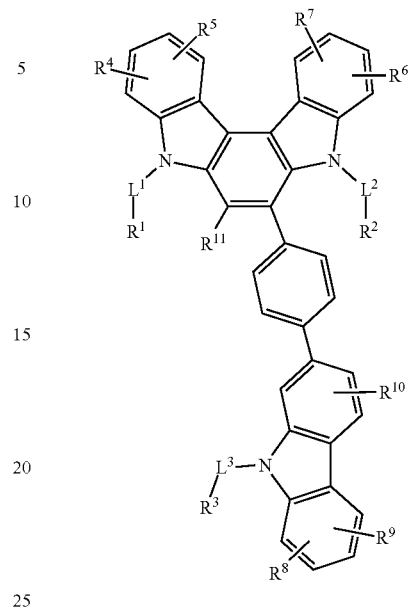
[Chemical Formula 5d]
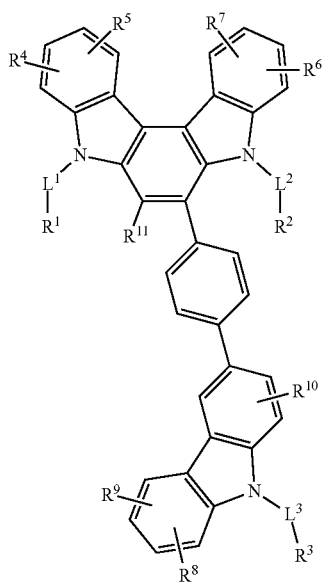
[Chemical Formula 5b]
In Chemical Formulae 5a to 5d, $L^1$ to $L^3$ and $R^1$ to $R^{11}$ are the same as described above.
The organic compound represented by Chemical Formula 6 may for example be represented by one of Chemical Formulae 6a to 6d according to bonding positions.

[Chemical Formula 6a]
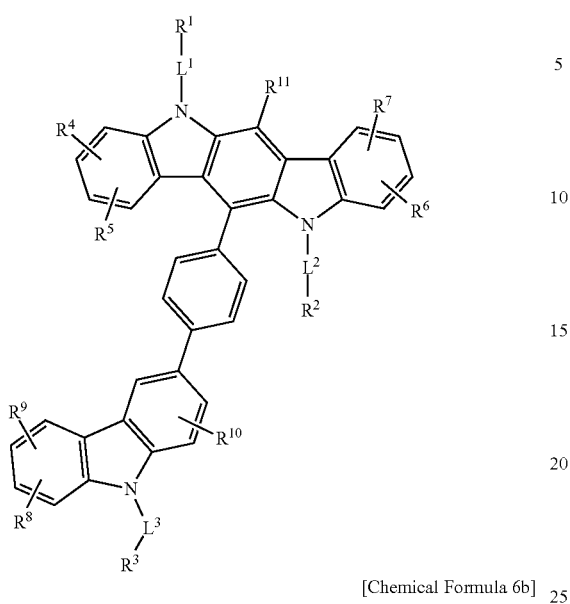
[Chemical Formula 6b]
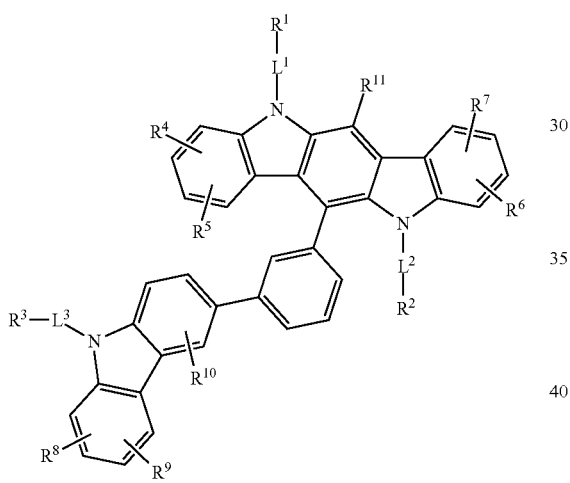
[Chemical Formula 6c]
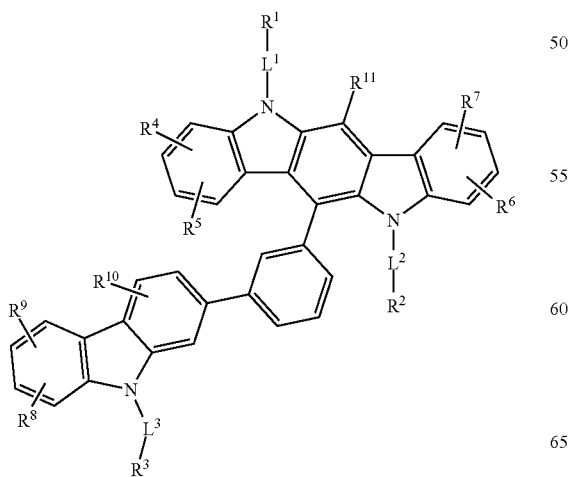
[Chemical Formula 6d]
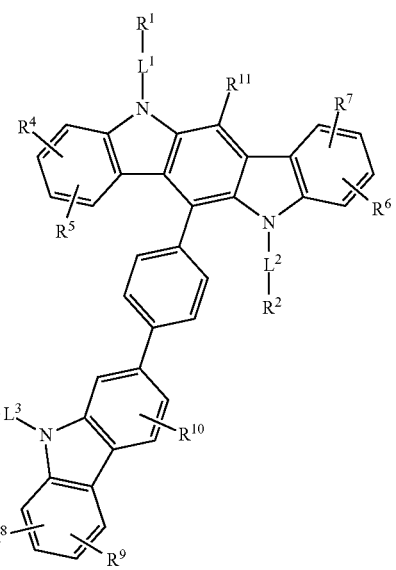
In Chemical Formulae 6a to 6d, $L^1$ to $L^3$ and $R^1$ to $R^{11}$ are the same as described above.
The organic compound represented by Chemical Formula 7 may for example be represented by one of Chemical Formulae 7a to 7h according to bonding positions.
[Chemical Formula 7a]
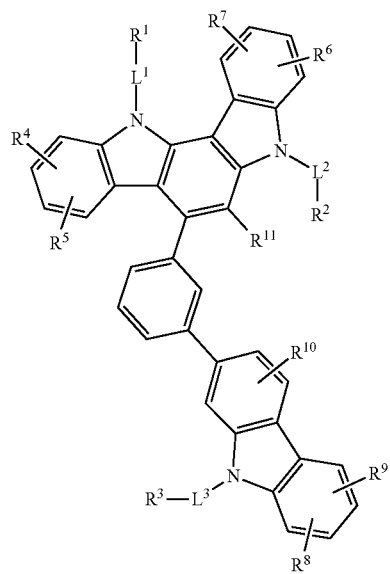

[Chemical Formula 7b]
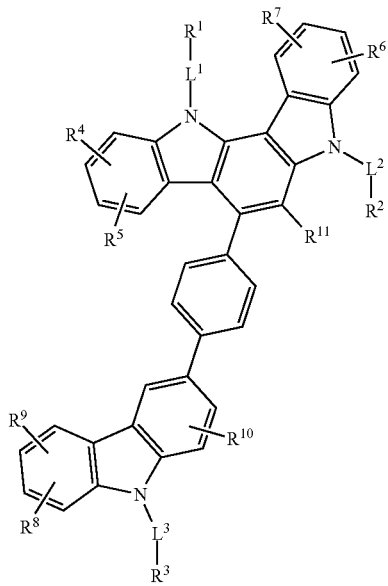
[Chemical Formula 7d]
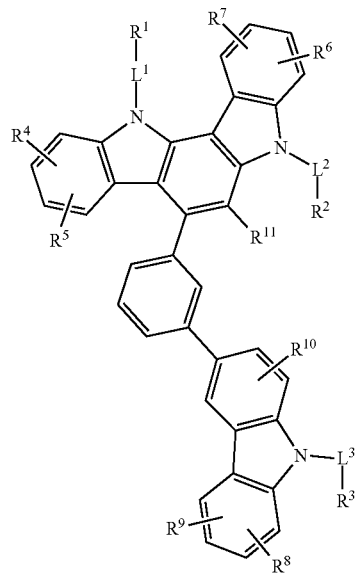
[Chemical Formula 7c]
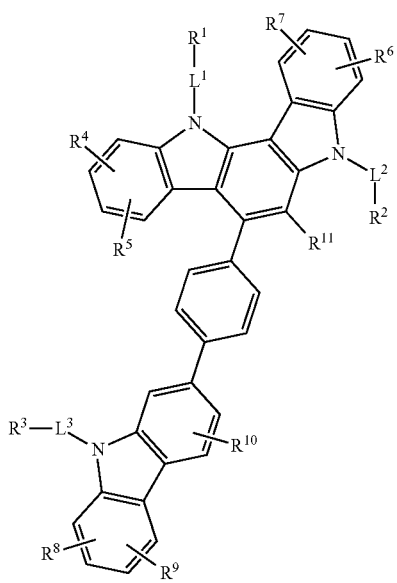
[Chemical Formula 7e]
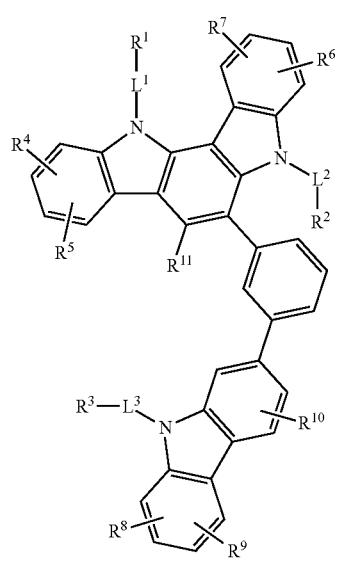

-continued

[Chemical Formula 7f]

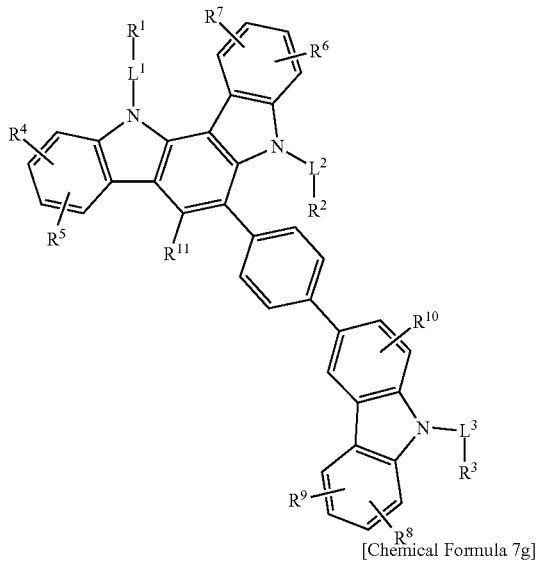

[Chemical Formula 7g]

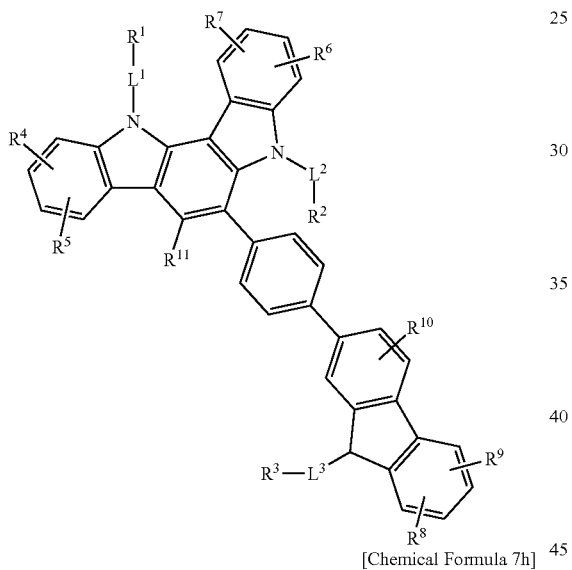

[Chemical Formula 7h]

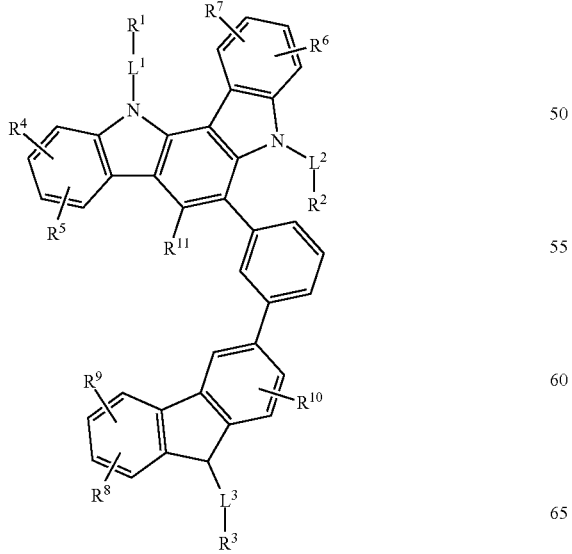

In Chemical Formulae 7a to 7h, $L^1$ to $L^3$ and $R^1$ to $R^{11}$ are the same as described above.

For example, in Chemical Formulae 4a to 4d, 5a to 5d, 6a to 6d, and 7a to 7h, $L^1$ to $L^3$ may independently be a single bond, a substituted or unsubstituted phenylene group, a substituted or unsubstituted naphthylene group, a substituted or unsubstituted biphenylene group, a substituted or unsubstituted terphenylene group, or a combination thereof.

For example, in Chemical Formulae 4a to 4d, 5a to 5d, 6a to 6d, and 7a to 7h, $R^1$ to $R^3$ may independently be a substituted or unsubstituted C6 to C30 aryl group.

For example, in Chemical Formulae 4a to 4d, 5a to 5d, 6a to 6d, and 7a to 7h, $R^1$ to $R^3$ may independently be a substituted or unsubstituted phenyl group, a substituted or unsubstituted biphenyl group, or a substituted or unsubstituted terphenyl group.

For example, in Chemical Formulae 4a to 4d, 5a to 5d, 6a to 6d, and 7a to 7h, at least one of $R^1$ to $R^3$ may be a substituted or unsubstituted phenyl group.

For example, in Chemical Formulae 4a to 4d, 5a to 5d, 6a to 6d, and 7a to 7h, at least two of $R^1$ to $R^3$ may be a substituted or unsubstituted phenyl group.

For example, in Chemical Formulae 4a to 4d, 5a to 5d, 6a to 6d, and 7a to 7h, $R^4$ to $R^{11}$ may independently be hydrogen or deuterium.

The organic compound may be for example compounds of Group 1, but is not limited thereto.

[Group 1]

[A-1]

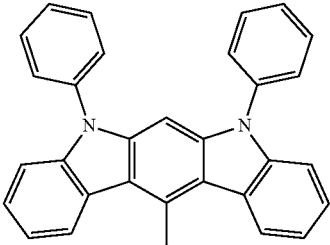
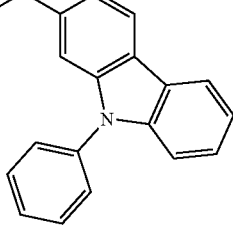

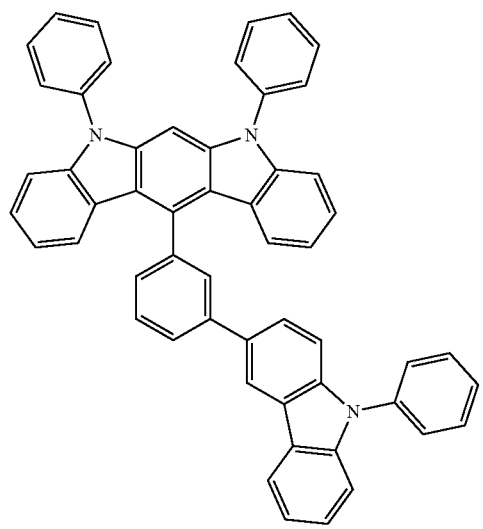
[A-2]
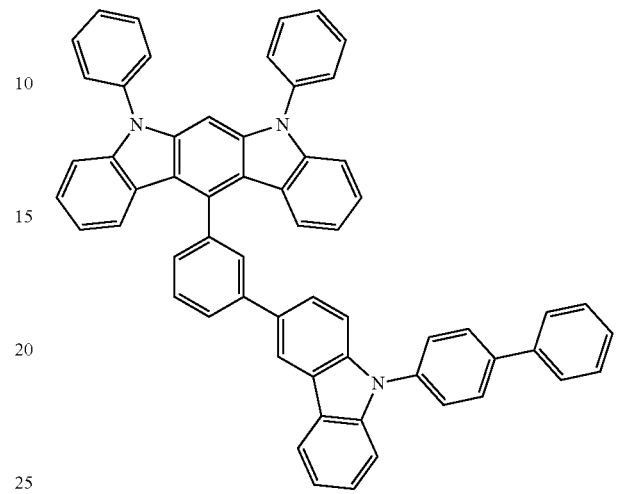
[A-4]
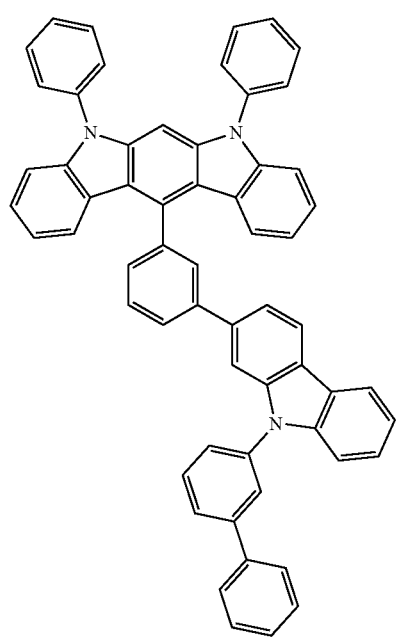
[A-3]
[A-5]

[A-6]
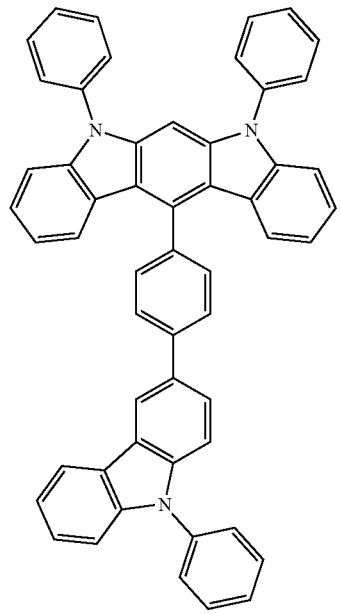
[A-7]
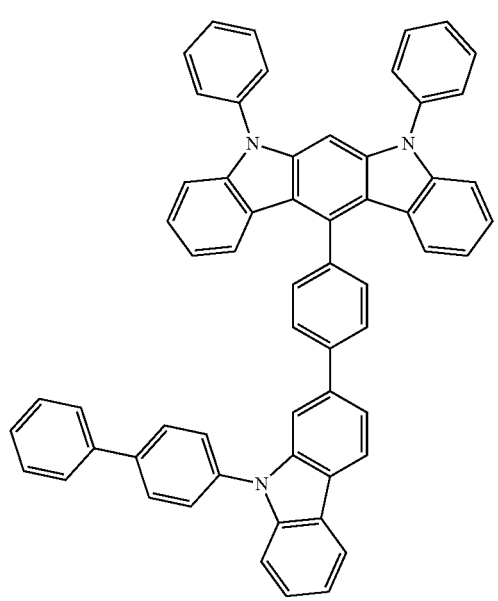
[A-8]
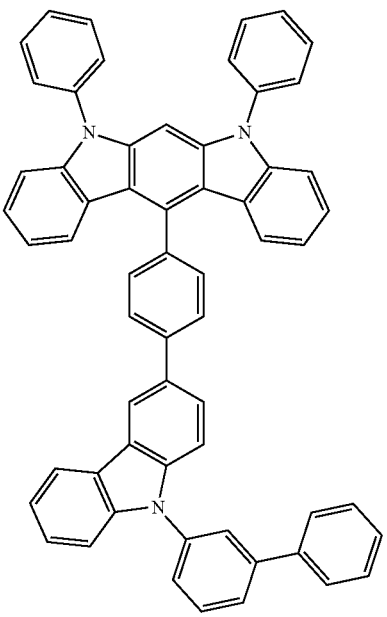
[C-1]
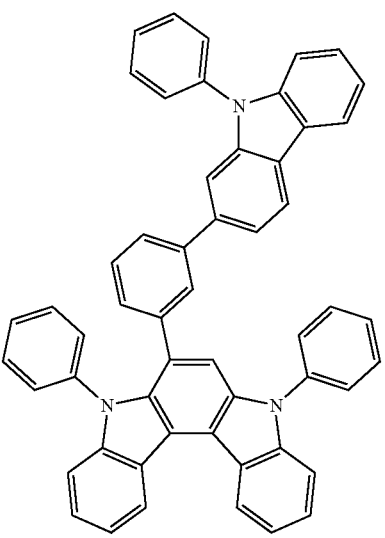
[C-2]
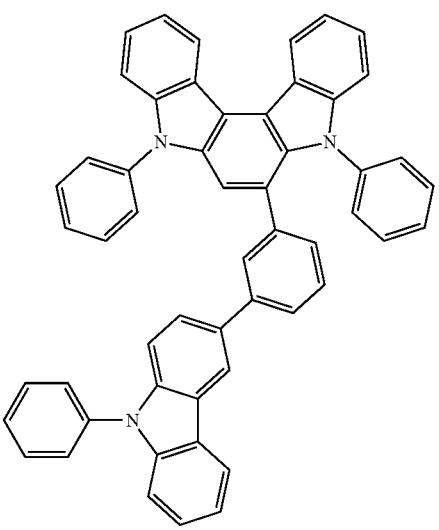

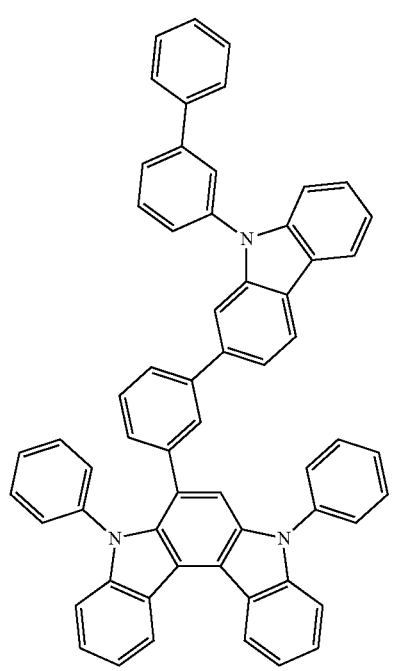
[C-3]
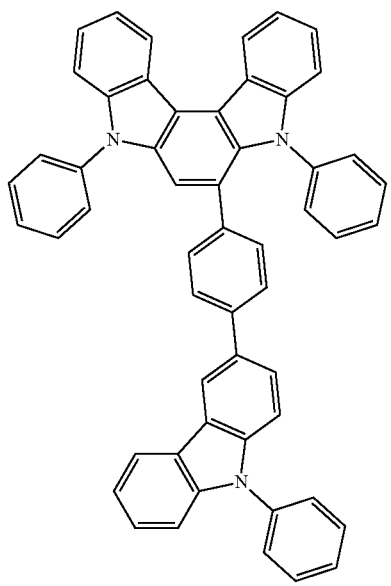
[C-5]
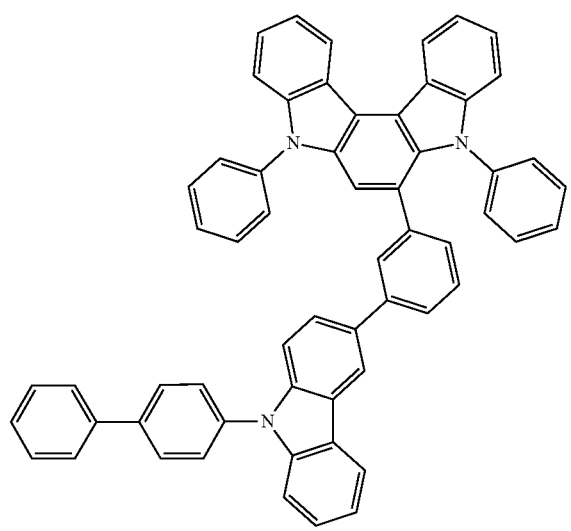
[C-4]
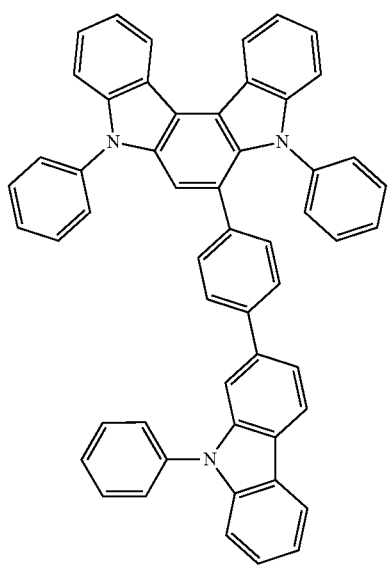
[C-6]

[C-7]
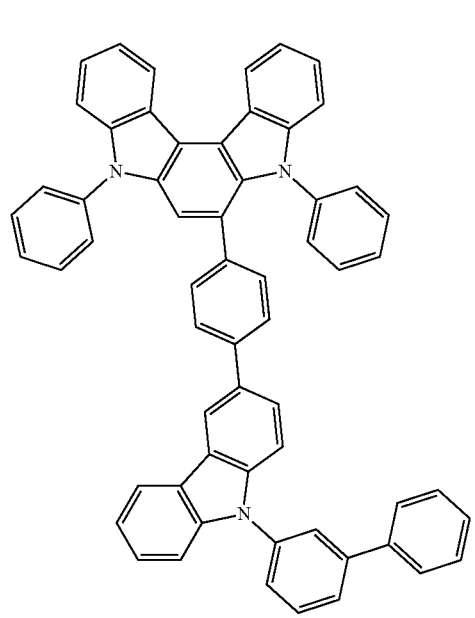
[C-8]
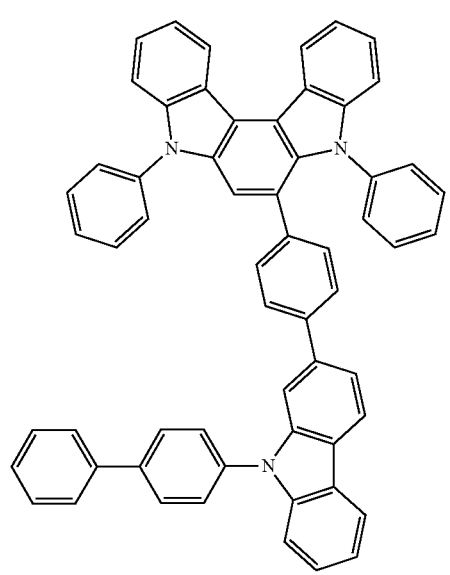
[D-1]
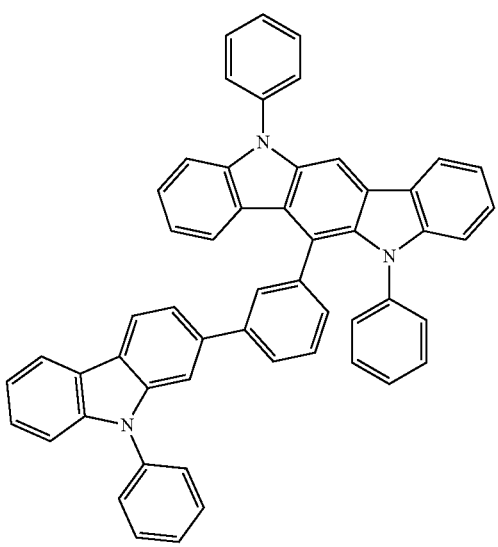
[D-2]
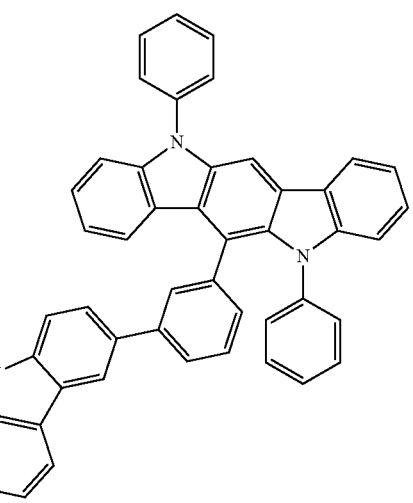

-continued
[D-3]
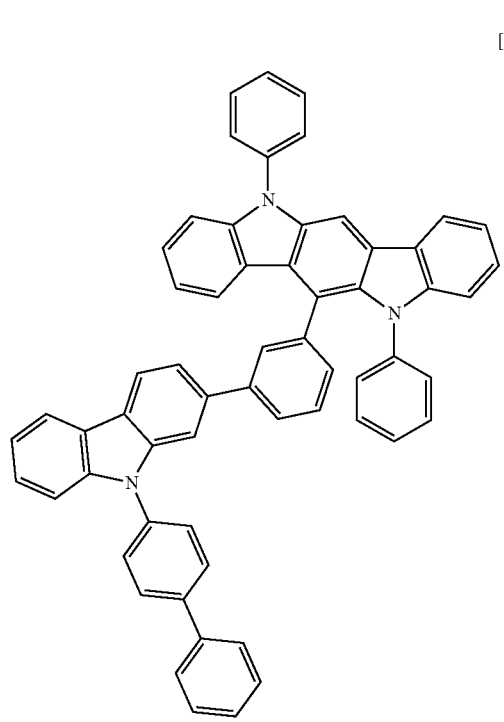
[D-5]
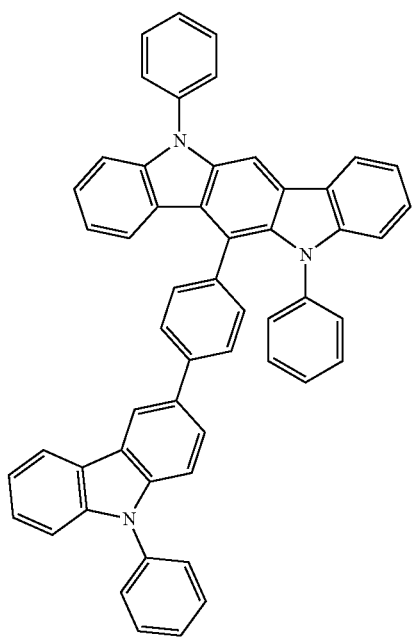
[D-4]
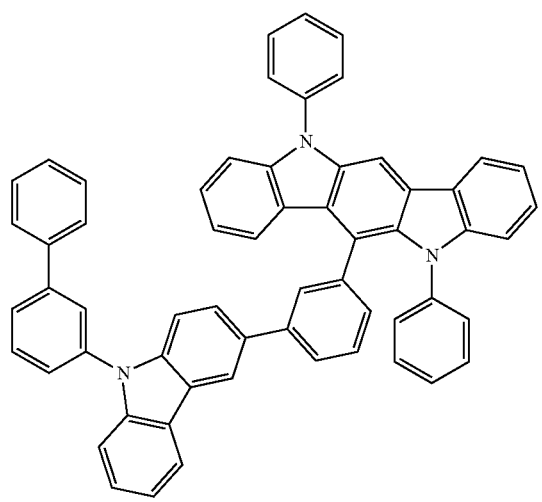
[D-6]
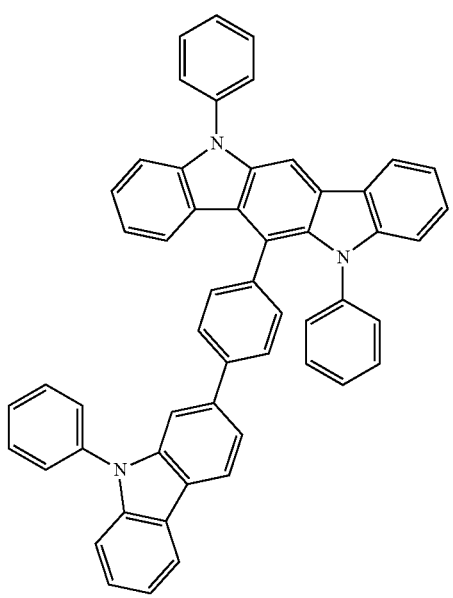

[D-7]
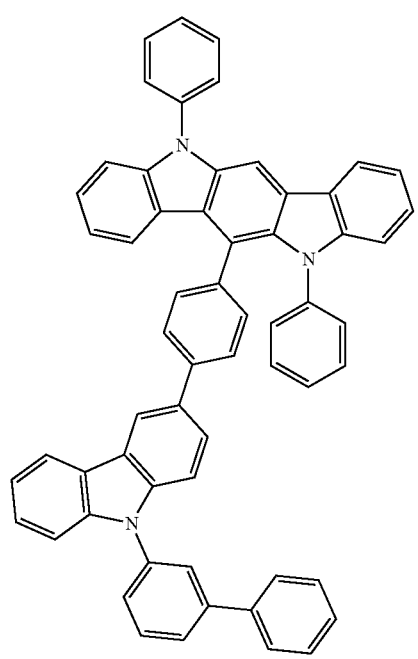
[D-8]
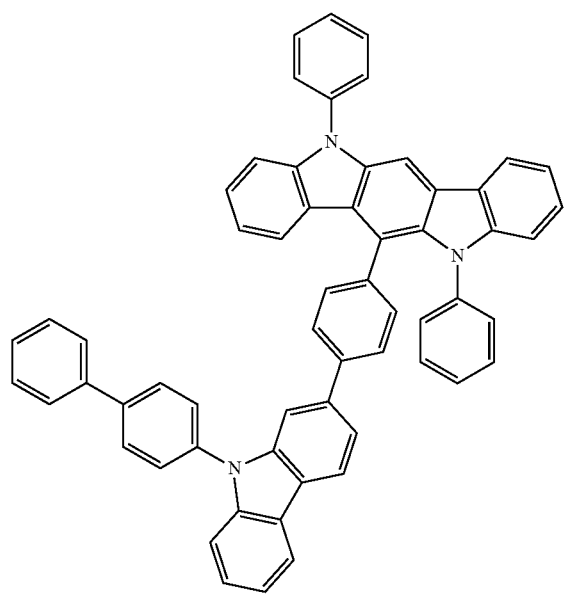
[E-1]
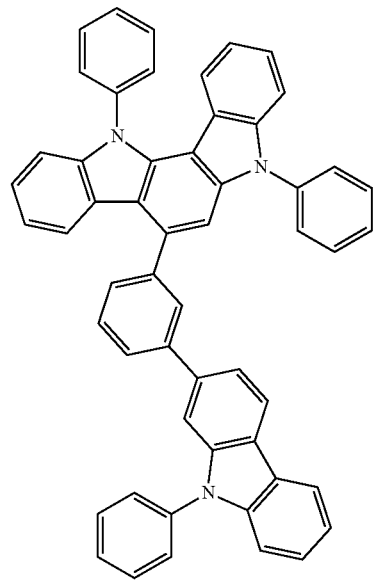
[E-2]
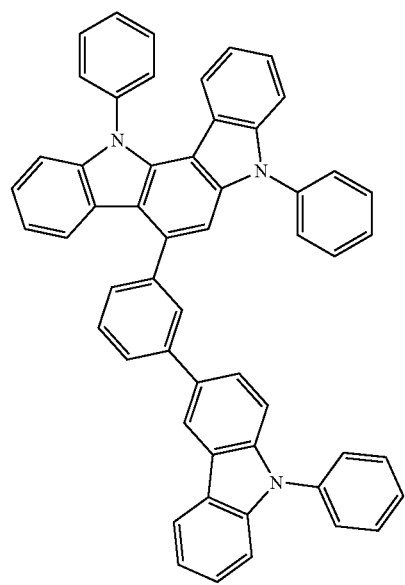

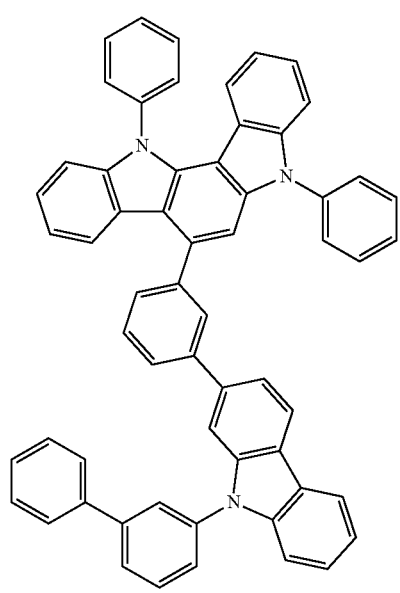
[E-3]
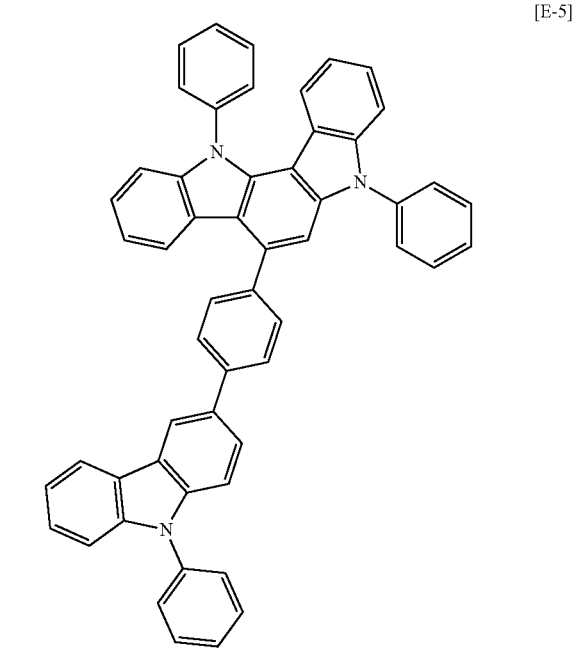
[E-5]
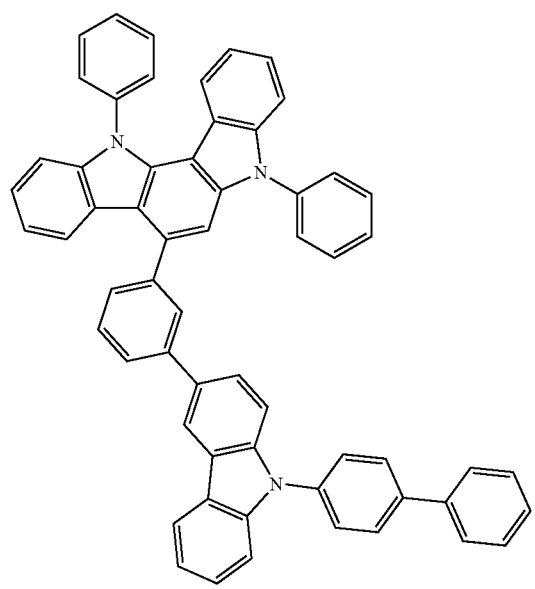
[E-4]
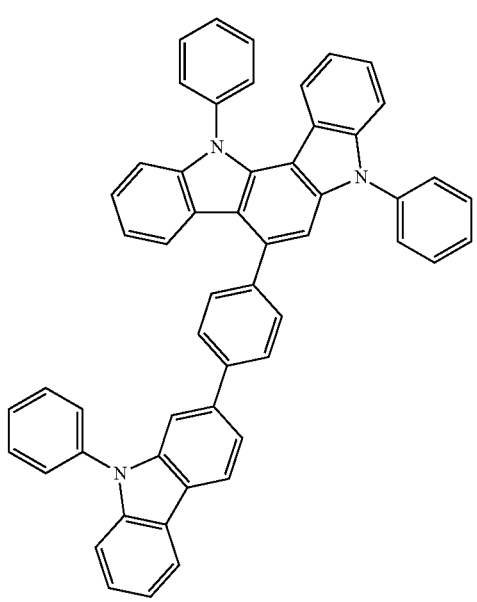
[E-6]

[E-7]
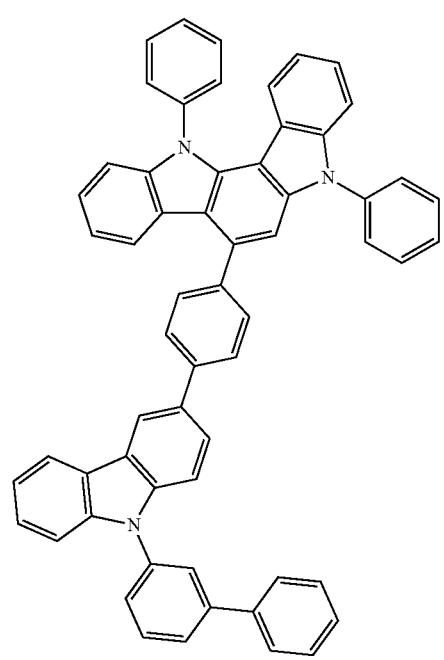
[F-1]
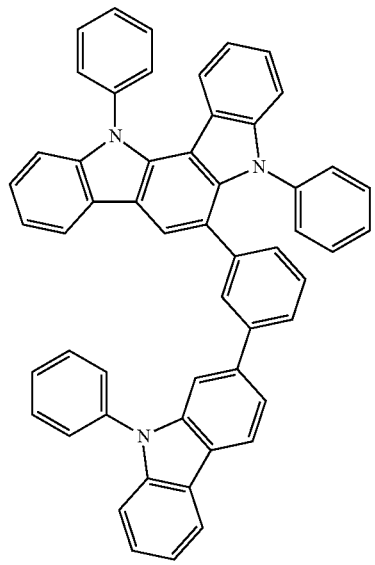
[E-8]
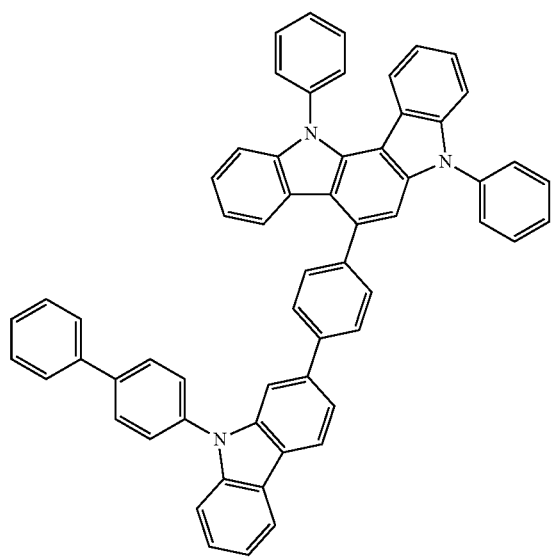
[F-2]
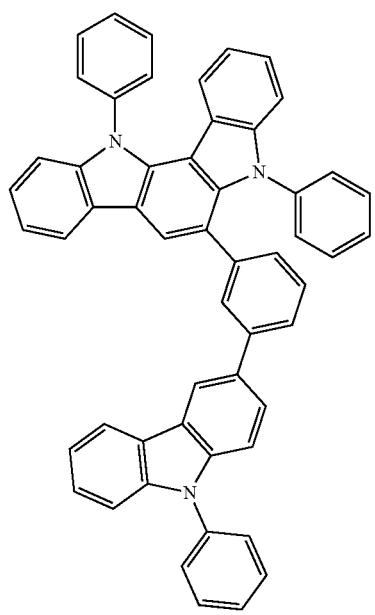

[F-3]
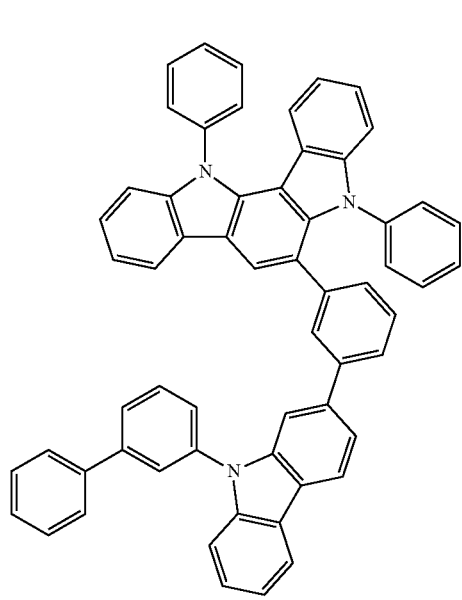
[F-4]
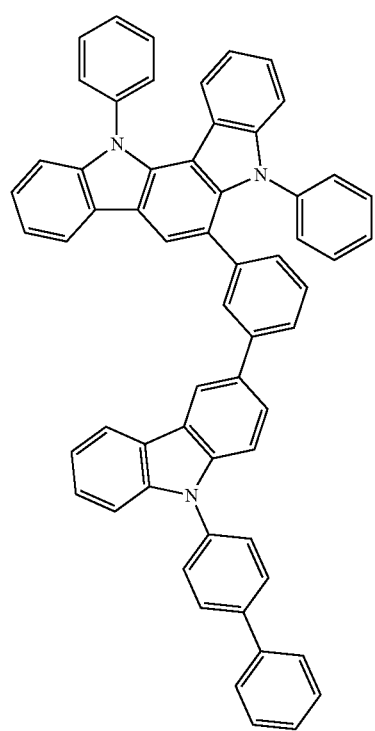
[F-5]
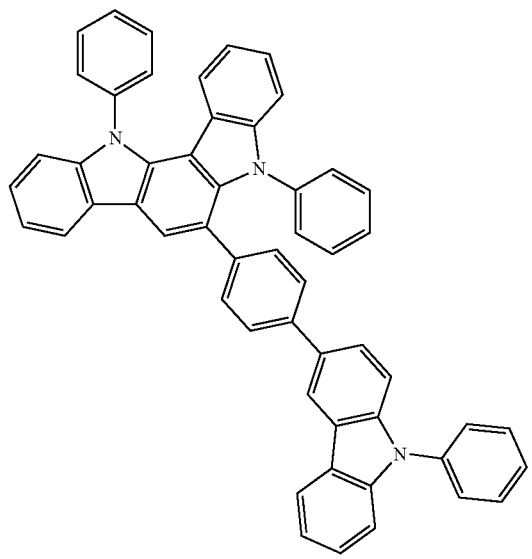
[F-6]
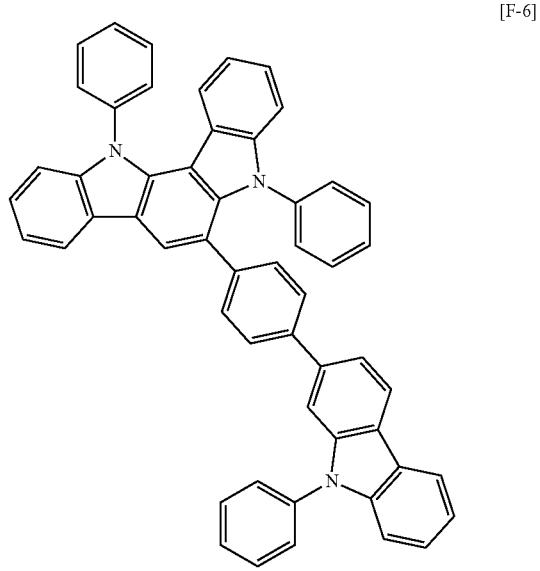

-continued

[F-7]

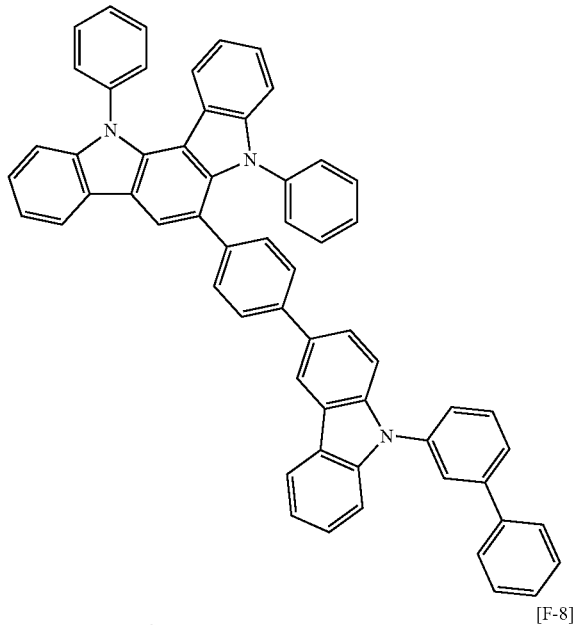

[F-8]

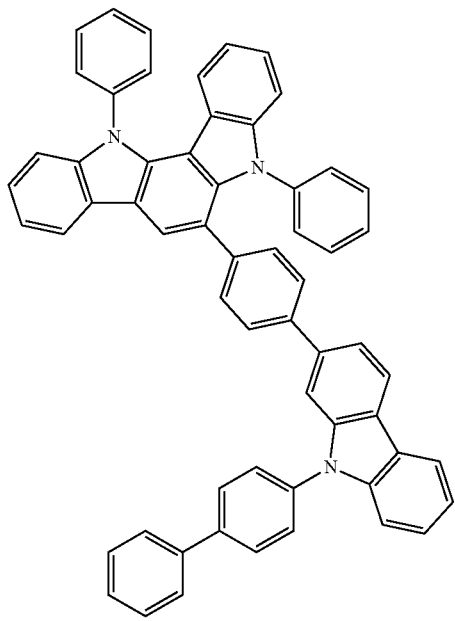

The organic compound may be applied to an organic electroluminescent device. The organic compound may be employed in an organic electroluminescent device alone or with other organic compounds.

Hereinafter, an organic optoelectronic device including the organic compound is described.

The organic electroluminescent device may be any device to convert electrical energy into photoenergy and vice versa without particular limitation, and may be, for example an organic photoelectric device, an organic light emitting diode, an organic solar cell, and an organic photo conductor drum.

The organic optoelectronic device includes an anode and a cathode facing each other and at least one organic layer disposed between the anode and the cathode, wherein the organic layer includes the organic compound.

For example, the organic layer may include a light emitting layer including the organic compound.

In one example of the present invention, the organic layer may include a light emitting layer including a plurality of hosts, the light emitting layer may include the organic compound as a first host and a compound including a substituted or unsubstituted triazinyl group or a substituted or unsubstituted pyrimidinyl group as a second host. Desirably, the light emitting layer may include the organic compound as a first host and a compound including a triazinyl group as a second host.

For example, a compound including a triazinyl group or a pyrimidinyl group as the second host may be a compound including a triazinyl group substituted with at least one C6 to C60 aryl group or a compound including a pyrimidinyl group substituted with at least one C6 to C60 aryl group.

For example, the second host may include a triazinyl group substituted with at least one selected from a phenyl group, a biphenyl group, a terphenyl group, a naphthyl group, an anthracenyl group, a triphenylene group, a quaterphenyl group, and a pentaphenyl group.

For example, the second host may include a pyrimidinyl group or a triazinyl group substituted with two or three C6 to C60 aryl groups, and desirably a pyrimidinyl group or a triazinyl group substituted with three C6 to C60 aryl groups. In addition, the aryl group may be substituted with a heteroaryl group or an aryl group.

In this way, the second host may provide a balance with the organic compound of the present invention having strong hole characteristics by using a compound including the triazinyl group or the pyrimidinyl group having strong electron characteristics, and thus may exhibit more improved device characteristics.

For example, the organic layer may include a light emitting layer, at least one auxiliary layer between the anode and the light emitting layer and/or the cathode and the light emitting layer, and the auxiliary layer may include the organic compound.

For example, the at least one auxiliary layer that is adjacent to the light emitting layer may include the organic compound.

For example, the organic layer may include a light emitting layer, a hole transport layer between the anode and the light emitting layer, a hole transport auxiliary layer between the light emitting layer and the hole transport layer and being adjacent to the light emitting layer, and the hole transport auxiliary layer includes the organic compound.

Herein, an organic light emitting diode as one example of an organic optoelectronic device is described referring to drawings.

FIG. 1 is a cross-sectional view showing an organic light emitting diode according to an embodiment.

Referring to FIG. 1, an organic light emitting diode 200 according to an embodiment includes an anode 110 and a cathode 120 and an organic layer 105 disposed between the anode 110 and the cathode 120.

The anode 110 may be made of a conductor having a large work function to help hole injection, and may be for example metal, metal oxide and/or a conductive polymer. The anode 110 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3- methylthiophene), poly(3,4-(ethylene-1,2-dioxy)thiophene) (PEDT), polypyrrole, and polyaniline, but is not limited thereto.

The cathode 120 may be made of a conductor having a small work function to help electron injection, and may be for example metal, metal oxide and/or a conductive polymer. The cathode 120 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes a light emitting layer 130.

The light emitting layer 130 may include the organic compound as a host, the organic compound may be included alone, at least two of the organic compounds may be mixed, or the organic compound may be mixed with other organic compounds.

For example, the organic compound may be used as a first host and may be mixed an organic compound that is different from the organic compound as a second host. For example, the second host may be an organic compound having electron characteristics, but is not limited thereto.

The light emitting layer 130 may further include a dopant. The dopant may be a red, green, or blue dopant, for example a blue dopant.

The dopant is mixed with the organic compound in a small amount to cause light emission, and may be generally a material such as a metal complex that emits light by multiple excitation into a triplet or more. The dopant may be for example an inorganic, organic, or organic/inorganic compound and one or more kinds thereof may be used.

The dopant is mixed with the organic compound in a small amount to cause light emission, and may be generally a material such as a metal complex that emits light by multiple excitation into a triplet or more. The dopant may be for example an inorganic, organic, or organic/inorganic compound and one or more kinds thereof may be used.

The light emitting layer 130 may be formed using a dry film formation method or a solution process. The dry film formation method may be, for example a chemical vapor deposition (CVD) method, sputtering, plasma plating, and ion plating, and two or more compounds may be simultaneously formed into a film or compound having the same deposition temperature may be mixed and formed into a film. The solution process may be, for example inkjet printing, spin coating, slit coating, bar coating and/or dip coating.

The organic layer 105 includes a hole auxiliary layer 140 disposed between the light emitting layer 130 and the anode 110. The hole auxiliary layer 140 improves hole injection and/or transport and inhibits and/or reduce electron injection between the anode 110 and the light emitting layer 130.

FIG. 2 is a cross-sectional view showing an organic light emitting diode according to another embodiment.

The hole auxiliary layer 140 includes the organic compound.

Referring to FIG. 2, an organic light emitting diode 300 according to an embodiment includes an anode 110 and a cathode 120 facing each other and an organic layer 105 disposed between the anode 110 and the cathode 120.

The organic layer 105 includes a light emitting layer 130 and a hole auxiliary layer 140 between the light emitting layer 130 and the anode 110.

The hole auxiliary layer 140 includes a hole transport layer 141 and a hole transport auxiliary layer 142.

The hole transport layer 141 may make hole transport from the anode 110 to the light emitting layer 130 easy. For example, the hole transport layer 141 may include a material having a HOMO energy level between a work function of a conductor of the anode 110 and a HOMO energy level of a material of the light emitting layer 130.

The hole transport layer 141 may include for example a compound represented by Chemical Formula 8 but is not particularly limited.

[Chemical Formula 8]

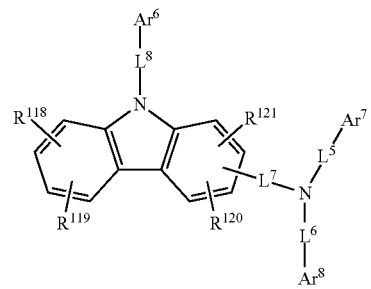

In Chemical Formula 8, $R^{118}$ to $R^{121}$ are independently hydrogen, deuterium, a substituted or unsubstituted C1 to C10 alkyl group, a substituted or unsubstituted C6 to C30 aryl group, a substituted or unsubstituted C2 to C30 heterocyclic group, or a combination thereof, $R^{118}$ and $R^{119}$ are independently present or forms a fused ring, $R^{120}$ and $R^{121}$ are independently present or forms a fused ring, $Ar^6$ to $Ar^8$ are independently a substituted or unsubstituted C6 to C30 aryl group or a substituted or unsubstituted C2 to C30 heterocyclic group, and $L^3$ to $L^8$ are independently a single bond, a substituted or unsubstituted C2 to C10 alkylene group, a substituted or unsubstituted C2 to C10 alkenylene group, a substituted or unsubstituted C2 to C10 alkynylene group, a substituted or unsubstituted C6 to C30 arylene group, divalent substituted or unsubstituted C2 to C30 heterocyclic group or a combination thereof.

For example, $Ar^6$ of Chemical Formula 8 may be a substituted or unsubstituted phenyl group, or a substituted or unsubstituted biphenyl group, BS $Ar^7$ and $Ar^8$ of Chemical Formula 8 may independently be one of a substituted or unsubstituted phenyl group, a substituted or unsubstituted biphenyl group, a substituted or unsubstituted fluorene group, a substituted or unsubstituted bisfluorene group, a substituted or unsubstituted triphenylene group, a substituted or unsubstituted anthracene group, a substituted or unsubstituted terphenyl group, a substituted or unsubstituted dibenzofuran group, or a substituted or unsubstituted dibenzothiophenyl group.

The hole transport auxiliary layer 142 is disposed to be adjacent to the light emitting layer 130 and may include the organic compound. The hole transport auxiliary layer 142 includes the above organic compound and thus may further effectively improve injection and/or transport of holes from the hole transport layer 141 on the interface of the light emitting layer 130 and the hole auxiliary layer 140 and block and/or reduce introduction of electrons therefrom and resultantly, improve efficiency and life-span of an organic light emitting diode.

In FIGS. 1 and 2, at least one electron auxiliary layer (not shown) as the organic layer 105 may be further included between the cathode 120 and the light emitting layer 130.

The organic light emitting diode may be applied to an organic light emitting display apparatus.

Mode for Invention

Hereinafter, the embodiments are illustrated in more detail with reference to examples. These examples, however, are not in any sense to be interpreted as limiting the scope of the invention.

Synthesis of Organic Compound

SYNTHESIS EXAMPLE 1

Synthesis of Compound A-5

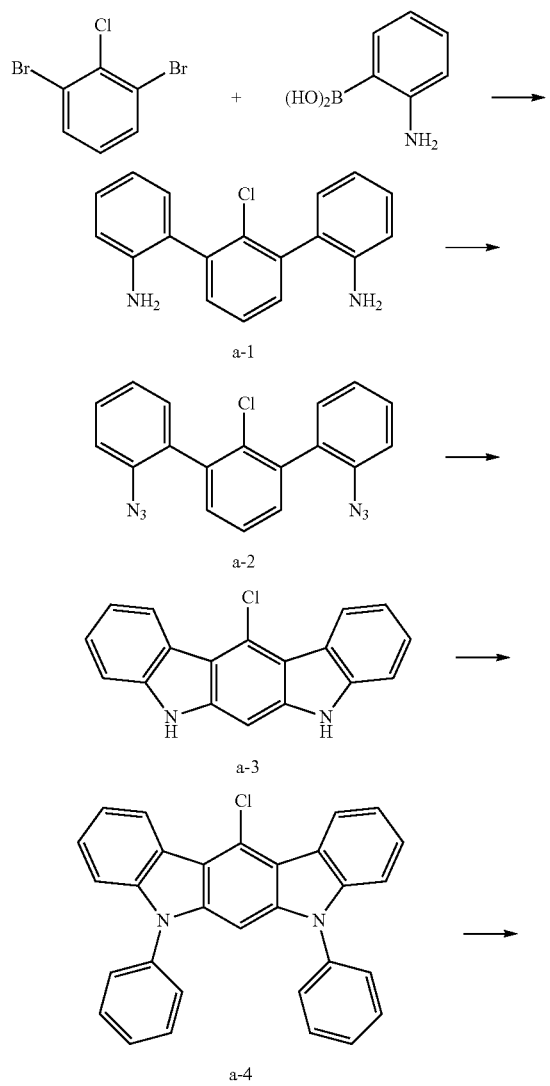

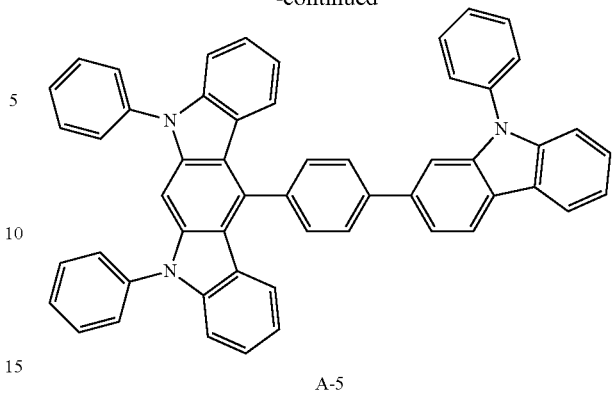

A-5

1 eq (45.5 g) of 1,3-dibromo-2-chloro-benzene, 2 eq (46.6 g) of 2-aminophenylboronic acid, 5 mol % (9.82 g) of tetrakis(triphenylphosphine)palladium (0) (Pd(PPh$_3$)$_4$), and 2 eq (47.0 g) of K$_2$CO$_3$ were suspended in toluene (12 times as much as a solid, 550 ml) and distilled water (5 times as much as K$_2$CO$_3$, 235 ml) and then, refluxed and stirred under a nitrogen flow for 18 hours. When a reaction was complete, toluene and distilled water were used for an extraction, an organic layer therefrom was dried with magnesium sulfate (MgSO$_4$) and filtered, and a filtrate was concentrated under a reduced pressure. After removing an organic solution, the rest thereof was silica gel columned with hexane:dichloromethane=7:3 (v/v), and a solid therefrom was recrystallized with dichloromethane and acetone to obtain Intermediate a-1 (37 g, Y=74%).

Step 2:

1 eq (36.5 g) of Intermediate a-1 was stirred with and dissolved in dioxane, and 7 eq (72 ml) of hydrochloric acid (35%) was slowly added thereto. Subsequently. 2 eq (18.9 g) of sodium nitrate and 2 eq (16.2 g) of sodium azide were dissolved in distilled water, and the solution was added to the mixture every hour. When a reaction was complete, the resultant was neutralized with NaOH, and a precipitate was obtained therefrom with methanol and then, washed with water and methanol and dried. A product therefrom was silica gel columned with hexane:dichloromethane=8:2 (v/v) to obtain Intermediate a-2 (35 g. Y=81%).

Step 3:

When a reaction was complete by refluxing and stirring 1 eq (35 g) of Intermediate a-2 with o-dichlorobenzene for 18 hours, dichloromethane/hexane were used for recrystallization after removing a solvent therefrom to obtain Intermediate a-3 (27.5 g, Y=94%).

Step 4:

1 eq (27.5 g) of Intermediate a-3, 2 eq (29.8 g) of bromobenzene, 2eq (36.4 g) of sodium t-butoxide, and 0.05 eq (4.34 g) of tris(dibenzylideneacetone)dipalladium (0) (Pd$_2$(dba)$_3$) were suspended in 330 ml 330 ml of toluene, 0.15 eq of tri-tertiarybutylphosphine was added thereto, and the mixture was refluxed and stirred for 18 hours. When the reaction was complete, the resultant was extracted with toluene and distilled water, then the organic layer was dried with magnesium sulfate and filtered and the filtrate was concentrated under reduced pressure. After removing an organic solution therefrom, the rest thereof was silica gel columned with hexane:dichloromethane=8:2 (v/v), and a solid therefrom was recrystallized with dichloromethane and ethyl acetate to obtain Intermediate a-4 (22 g, Y=52%).

Step 5:

1 eq (22 g) of Intermediate a-4, 1 eq (18 g) of 2-(4-phenylboronic acid)-9-phenyl-carbazole, 5 mol % (2.27 g) of Pd$_2$(dba)$_3$, and 2 eq (32.4 g) of Cs$_2$CO$_3$ were suspended in 250 ml of toluene, 0.15 eq (1.5 g) of tri-tertiarybutylphosphine was added thereto, and the mixture was refluxed and stirred under a nitrogen flow for 18 hours. When the reaction was complete, the resultant was extracted with toluene and distilled water, then the organic layer was dried with magnesium sulfate and filtered and the filtrate was concentrated under reduced pressure. Subsequently, after removing an organic solution, the rest thereof was silica gel columned with hexane:dichloromethane=8:2 (v/v) and recrystallized with dichloromethane and ethyl acetate to obtain Compound A-5 (12 g, Y=33%). LC-Mass measurement (theoretical value: 725.28 g/mol, measured value: M=725 g/mol)

SYNTHESIS EXAMPLE 2

Synthesis of Compound A-6

1 eq (22 g) of Intermediate a-4, 1 eq (18 g) of 3-(4-phenylboronic acid)-9-phenyl-carbazole, 5 mol % (2.27 g) of Pd$_2$(dba)$_3$, and 2 eq (32.4 g) of Cs$_2$CO$_3$ were suspended in 250 ml of toluene, 0.15 eq (1.5 g) of tri-tertiarybutylphosphine was added thereto, and the mixture was refluxed and stirred under a nitrogen flow for 18 hours. When a reaction was complete, toluene and distilled water were used for an extraction, an organic layer therefrom was dried with magnesium sulfate and filtered, and a filtrate was concentrated under a reduced pressure. After removing an organic solution, the rest thereof was silica gel columned with hexane:dichloromethane=8:2 (v/v), and a solid therefrom was recrystallized with dichloromethane and ethyl acetate to obtain Compound A-6 (14.5 g, Y=40%).

LC-Mass measurement (theoretical value: 725.28 g/mol, measured value: M=725 g/mol)

[A-6]

SYNTHESIS EXAMPLE 3

Synthesis of Compound C-5

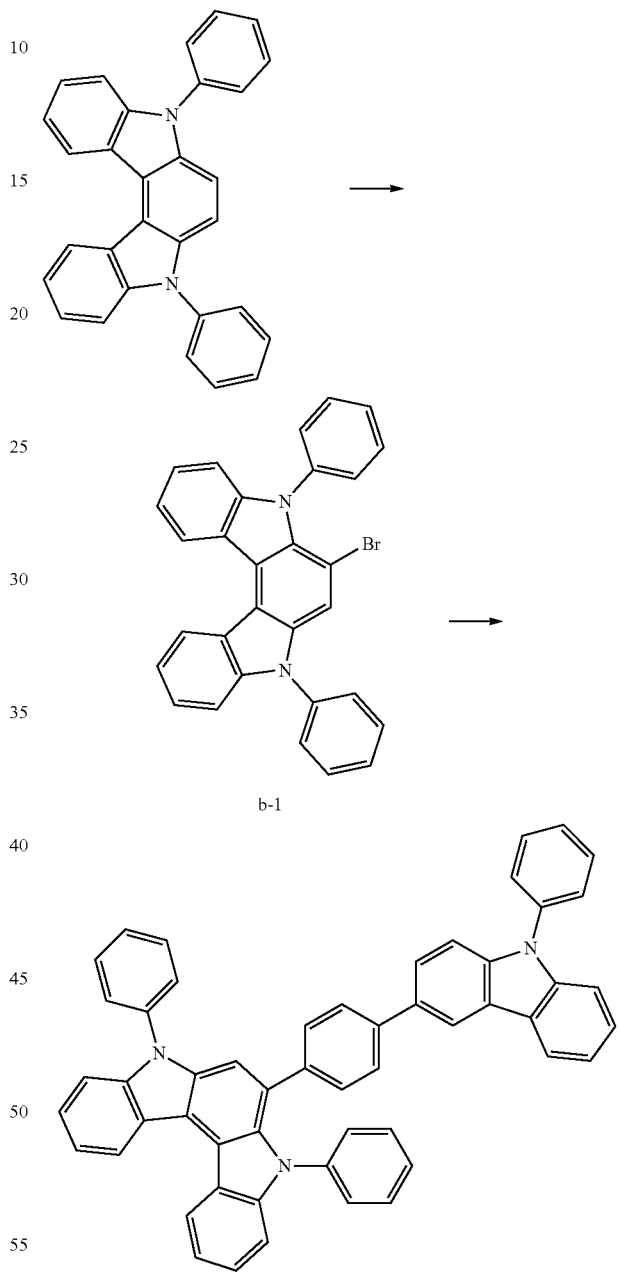

[Reaction Scheme 2]

b-1

C-5

Step 1:

25.1 g of indolo[2,3-c]carbazole,5,8-dihydro-5,8-diphenyl and 0.95 eq (10.4 g) of N-bromosuccin imide (NBS) were suspended in 250 ml of chloroform and then, stirred under a nitrogen flow for 8 hours. When a reaction was complete, an aqueous layer was removed, an organic layer was filtered, and a filtrate was recrystallized with acetone to obtain Intermediate b-1 (27.6 g, 92%).

Step 2:

1 eq (13.4 g) of Intermediate b-1, 1 eq (10.0 g) of 3-(4-phenylboronic acid)-9-phenyl-carbazole, 5 mol % (1.6 g) of Pd(PPh₃)₄DeletedTextsand 2 eq (7.6 g) of K₂CO₃ were suspended in toluene (12 times as much as a solid, 160 ml), and distilled water (5 times as much as K₂CO₃, 40 ml) and then, refluxed and stirred under a nitrogen flow for 18 hours. When a reaction was complete, toluene and distilled water were used for an extraction, then, an organic layer therefrom was with magnesium sulfate (MgSO₄) and filtered, and a filtrate therefrom was concentrated under a reduced pressure. After removing an organic solution, the rest thereof was silica gel column with hexane:dichloromethane=7:3 (v/v), and solid therefrom was recrystallized with dichloromethane and acetone to obtain Compound C-5 (14.1 g, Y=71%).

LC-Mass measurement (theoretical value: 725.28 g/mol, measured value: M=725 g/mol)

SYNTHESIS EXAMPLE 4

Synthesis of Compound D-5

[Reaction Scheme 3]

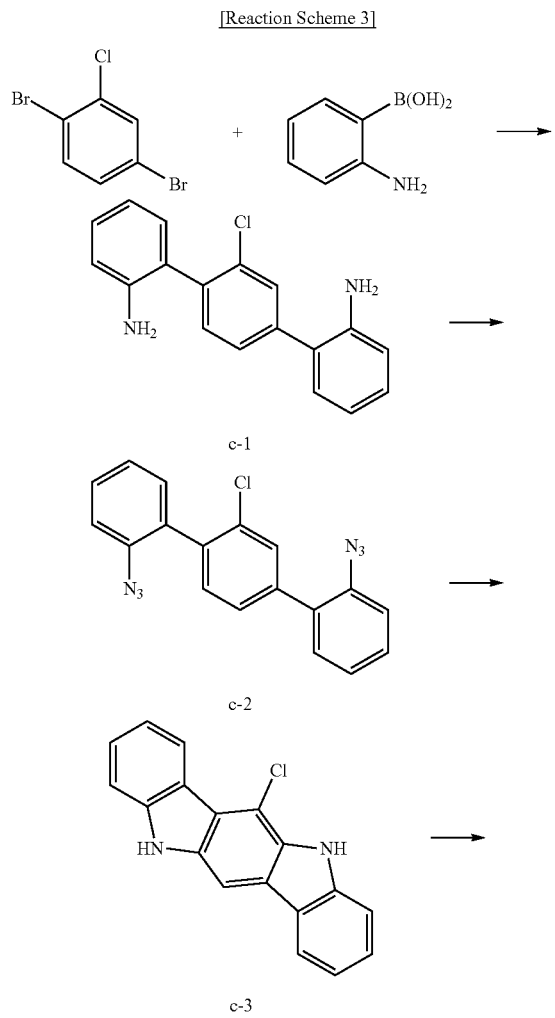

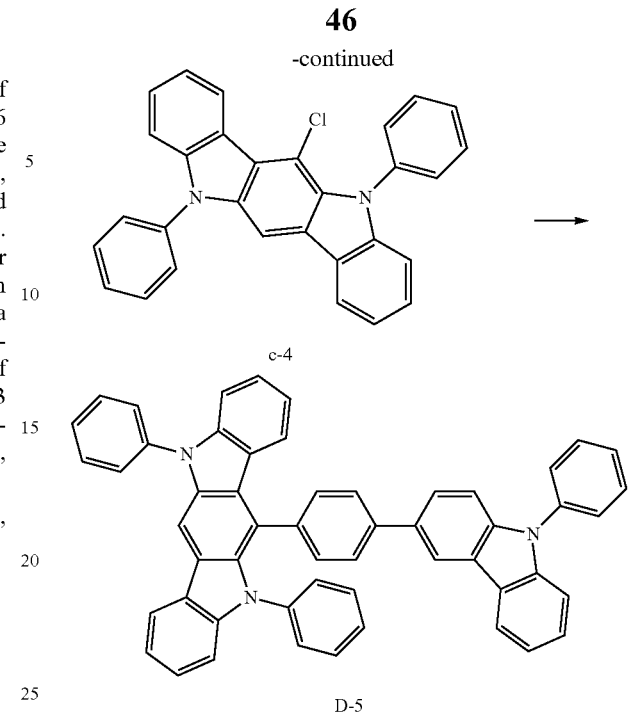

D-5

1 eq (45.8 g) of 1,4-dibromo-2-chloro-benzene, 2 eq (46.5 g) of 2-aminophenylboronic acid, 5 mol % (9.8 g) of Pd(PPh₃)₄, and 2 eq (46.9 g) of K₂CO₃ were suspended in toluene (12 times as much as a solid, 550 ml) and distilled water (5 times as much as K₂CO₃, 235 ml) and then, refluxed and stirred under a nitrogen flow for 18 hours. When a reaction was complete, toluene and distilled water were used for an extraction, an organic layer therefrom was dried with magnesium sulfate (MgSO₄) and filtered, and a filtrate therefrom was concentrated under a reduced pressure. After removing an organic solution therefrom, the rest thereof was silica gel columned with hexane:dichloromethane=7:3 (v/v), and a solid therefrom was recrystallized with dichloromethane and acetone to obtain Intermediate c-1 (23.5 g, Y=47%).

Step 2:

1 eq (23.5 g) of Intermediate c-1 was stirred and dissolved in dioxane, and 7 eq (50 ml) of hydrochloric acid (35%) was slowly added thereto. Subsequently, 2 eq (12.1 g) of sodium nitrate and 2 eq (10.4 g) of sodiumazide were dissolved in distilled water, and a solution therefrom was added to the above mixture by every hour. When a reaction was complete, the resultant was neutralized with NaOH, and a precipitate obtained with methanol was washed with water and methanol and then, dried. A product therefrom was silica gel-columned with hexane:dichloromethane=8:2 (v/v) to obtain Intermediate c-2 (22.6 g, Y=82%).

Step 3:

When 1 eq (22.6 g) of Intermediate c-2 was refluxed and stirred with o-dichlorobenzene for 18 hours, a solvent was removed with dichloromethane/hexane and recrystallizated to obtain Intermediate c-3 (15.3, Y=81%).

Step 4:

1 eq (15.3 g) of Intermediate c-3 was suspended in 2 eq (16.5 g) of bromobenzene, 2 eq (20.2 g) of sodium t-butoxide, 0.05 eq (2.4 g) of Pd₂(dba)₃ was suspended in 330 ml of toluene, 0.15 eq (1.6 g) of tri-tertiarybutylphosphine was added thereto for 18 hours and then, refluxed and stirred. When the reaction was complete, the resultant was extracted with toluene and distilled water, then the organic layer was dried with magnesium sulfate and filtered and the filtrate was concentrated under reduced pressure. After removing an organic solution therefrom, the rest thereof was silica gel columned with hexane:dichloromethane=8:2 (v/v), and a solid therefrom was recrystallized with dichloromethane and ethyl acetate to obtain Intermediate c-4 (10.8 g, Y=46%).

Step 5:

1 eq (10.8 g) of Intermediate c-4, 1 eq (8.9 g) of 3-(4-phenylboronic acid)-9-phenyl-carbazole, 5 mol % (1.1 g) of Pd$_2$(dba)$_3$, and 2 eq (15.9 g) of Cs$_2$CO$_3$ were suspended in 120 ml of toluene, 0.15 eq (0.75 g) of tri-tertiary-butylphosphine was added thereto, and the obtained mixture was refluxed and stirred under a nitrogen flow for 18 hours. When a reaction was complete, toluene and distilled water were used for an extraction, and an organic layer therefrom was dried with magnesium sulfate, filtered, and concentrated under a reduced pressure. After removing an organic solution, the rest thereof was silica gel columned with hexane:dichloromethane=7:3 (v/v), and a solid therefrom was recrystallized with dichloromethane and ethyl acetate to obtain Compound D-5 (9.3 g, Y=53%).

LC-Mass measurement (theoretical value: 725.28 g/mol, measured value: M=725 g/mol)

SYNTHESIS EXAMPLE 5

Synthesis of Compound D-7

1 eq (8.3 g) of Intermediate c-4, 1 eq (8.2 g) of 3-(4-phenylboronic acid)-9-(biphenyl-3)-carbazole, 5 mol % (0.86 g) of Pd$_2$(dba)$_3$, and 2 eq (12.2 g) of Cs$_2$CO$_3$ were suspended in 100 ml of toluene, 0.15 eq (0.57 g) of tri-tertiarybutylphosphine was added thereto, and the obtained mixture was refluxed and stirred under a nitrogen flow for 18 hours. When the reaction was complete, the resultant was extracted with toluene and distilled water, then the organic layer was dried with magnesium sulfate and filtered and the filtrate was concentrated under reduced pressure. After removing an organic solution, the rest thereof was silica gel columned with hexane:dichloromethane=7:3 (v/v), and a solid therefrom was recrystallized with dichloromethane and ethyl acetate to obtain Compound D-7 (5.6 g, Y=37%).

LC-Mass measurement (theoretical value: 801.31 g/mol, measured value: M=801 g/mol)

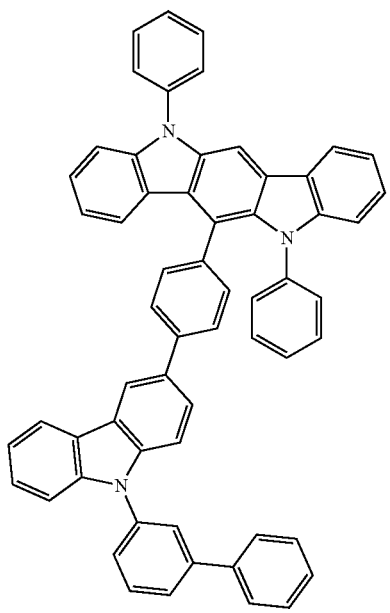

[D-7]

SYNTHESIS EXAMPLE 6

Synthesis of Compound F-2

[Reaction Scheme 4]

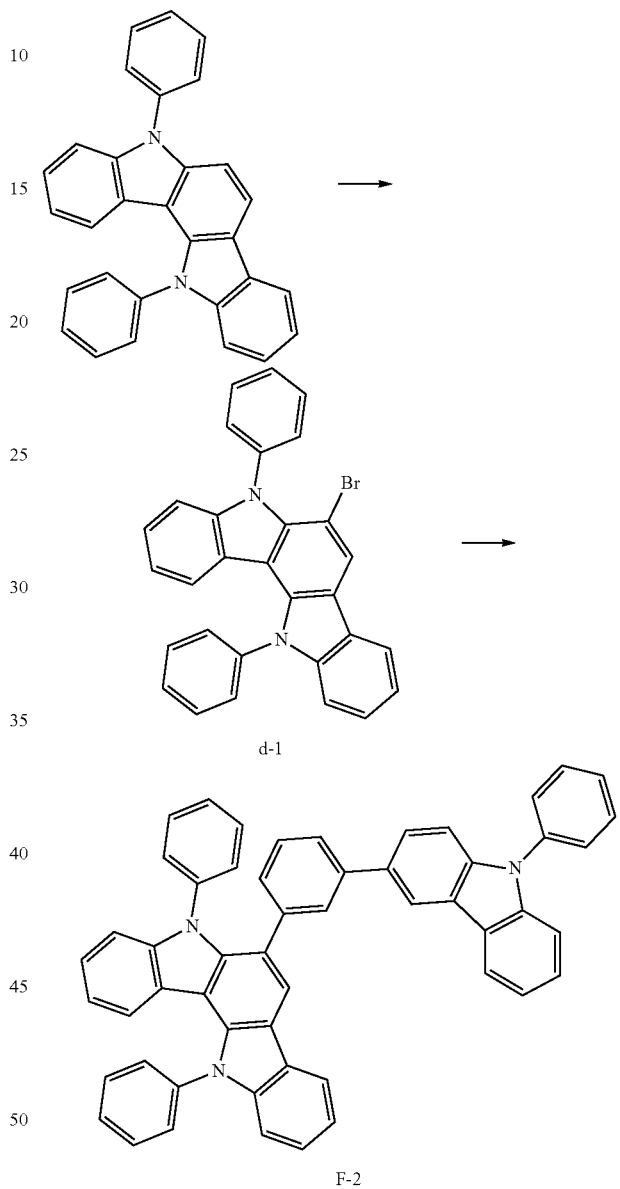

Step 1:

Indolo[3,2-a]carbazole, 25.1 g of 5,12-dihydro-5,12-diphenyl, and 0.95 eq (10.4 g) of N-bromosuccinimide (NBS) were suspended in 200 ml of chloroform and then, stirred under a nitrogen flow for 8 hours. When a reaction was complete, the resultant was washed with water, an aqueous layer was removed therefrom, an organic layer alone was filtered, and a filtrate was recrystallized with acetone to obtain Intermediate d-1 (28.7 g, 96%).

Step 2:

1 eq (14.1 g) of Intermediate d-1, 1 eq (10.5 g) of 3-(3-phenylboronic acid)-9-phenyl-carbazole, 5 mol % (1.7 g) of Pd(PPh$_3$)$_4$, and 2 eq (8.0 g) of K$_2$CO$_3$ were suspended in toluene (12 times as much as a solid, 170 ml) and distilled water (5 times as much as an amount of K₂CO₃, 40 ml) and then, refluxed and stirred under a nitrogen flow for 18 hours. When a reaction was complete, toluene and distilled water were used for an extraction, an organic layer therefrom was dried with magnesium sulfate (MgSO₄) and filtered, and a filtrate therefrom was concentrated under a reduced pressure. After removing an organic solution, the rest therefof was silica gel columned with hexane:dichloromethane=7:3 (v/v), and a solid therefrom was recrystallized with dichloromethane and acetone to obtain Compound F-2 (15.5 g, Y=74%).

LC-Mass measurement (theoretical value: 725.28 g/mol, measured value: M=725 g/mol)

SYNTHESIS EXAMPLE 7

Synthesis of Compound F-5

1 eq (14.1 g) of Intermediate d-1, 1 eq (10.5 g) of 3-(4-phenylboronic acid)-9-phenyl-carbazole, 5 mol % (1.7 g) of Pd(PPh₃)₄, and 2eq (8.0 g) K₂CO₃ were suspended in toluene (12 times as much as a solid, 170 ml) and distilled water (5 times as much as an amount of K₂CO₃, 40 ml) and then, refluxed and stirred under a nitrogen flow for 18 hours. When a reaction was complete, toluene and distilled water were used for an extraction, and an organic layer therefrom was dried with magnesium sulfate (MgSO₄) and filtered, and a filtrate was concentrated under a reduced pressure. After removing an organic solution therefrom, the rest thereof was silica gel columned with hexane:dichloromethane=7:3 (v/v), and a solid therefrom was recrystallized with dichloromethane and acetone to obtain Compound F-5 (17.3 g, Y=82%).

LC-Mass measurement (theoretical value: 725.28 g/mol, measured value: M=725 g/mol)

[F-5]

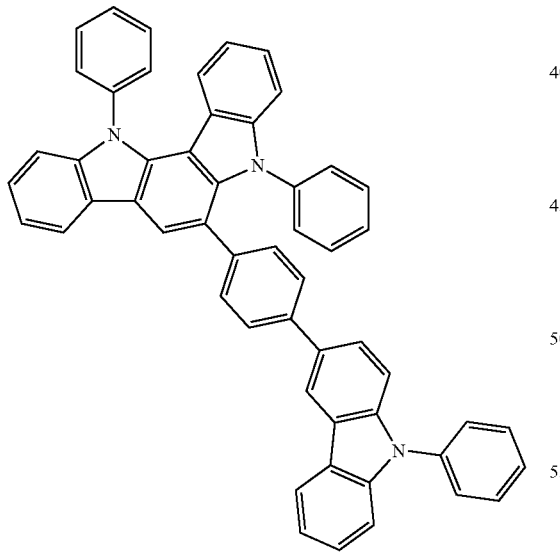

COMPARATIVE SYNTHESIS EXAMPLE 1

Synthesis of Host-1

Step 1:
Indolo[2,3-a]carbazole, 25.1 g of 11,12-dihydro-11,12-diphenyl, and 0.95 eq (10.4 g) of N-bromosuccin imide (NBS) were suspended in 200 ml of chloroform and stirred under a nitrogen flow for 8 hours. When a reaction was complete, a resultant was washed with water, an aqueous layer was removed therefrom, an organic layer alone was filtered therefrom, and a filtrate was recrystallized with acetone to obtain Intermediate h-1 (28.5 g, 95%).

Step 2:
1 eq (14.1 g) of Intermediate h-1, 1 eq (10.5 g) of 3-(4-phenylboronic acid)-9-phenyl-carbazole, 5 mol % (1.7 g) of Pd(PPh₃)₄, and 2 eq (8.0 g) of K₂CO₃ were suspended in toluene (12 times as much as a solid, 170 ml) and distilled water (5 times as much as an amount of K₂CO₃, 40 ml) under a nitrogen flow for 18 hours and then, refluxed and stirred. When a reaction was complete, toluene and distilled water were used for an extraction, an organic layer therefrom was dried and filtered with magnesium sulfate (MgSO₄), and a filtrate was concentrated under a reduced pressure. After removing an organic solution therefrom, the rest thereof was silica gel columned with hexane:dichloromethane=8:2 (v/v), and a solid produced therein was recrystallized with dichloromethane and acetone to obtain Compound Host-1 (16.5 g, Y=79%). LC-Mass measurement (theoretical value: 725.28 g/mol, measured value: M=725 g/mol)

HOST-1

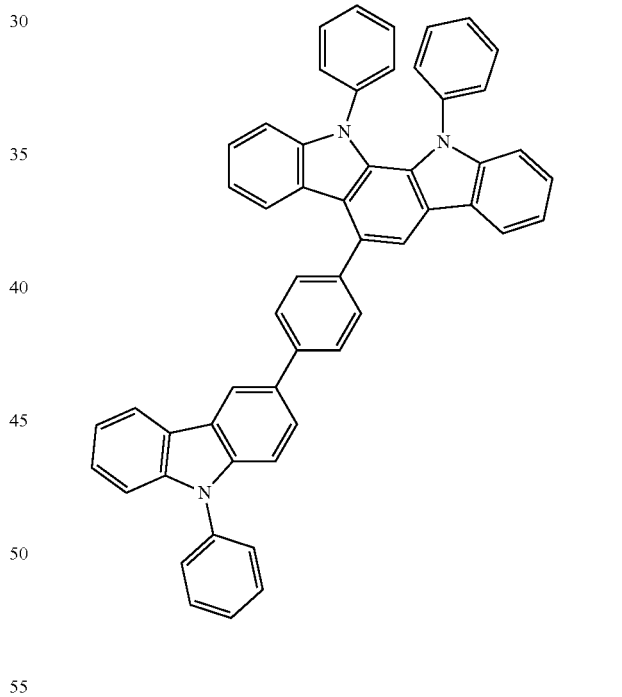

COMPARATIVE SYNTHESIS EXAMPLE 2

Synthesis of Host-2

1 eq (15.0 g) of Intermediate h-1 according to step 1 of Comparative Synthesis Example 1, 1 eq (8.8 g) of 3-boronic acid-9-phenyl-carbazole, 5 mol % (1.8 g) of Pd(PPh₃)₄, and 2 eq (8.5 g) of K₂CO₃ were suspended in toluene (12 times as much as a solid, 180 ml) and distilled water (5 times as much as an amount of K₂CO₃, 45 ml) and refluxed and stirred under a nitrogen flow for 18 hours. When a reaction was complete, toluene and distilled water were used for an extraction, and an organic layer therefrom was dried and filtered with magnesium sulfate (MgSO$_4$) and then, concentrated under a reduced pressure. After removing an organic solution, the rest thereof was silica gel columned with hexane:dichloromethane=8:2 (v/v), and a solid produced therein was recrystallized with dichloromethane and acetone to obtain Compound Host-2 (14.3 g, Y=72%).

LC-Mass measurement (theoretical value: 649.25 g/mol, measured value: M=649 g/mol)

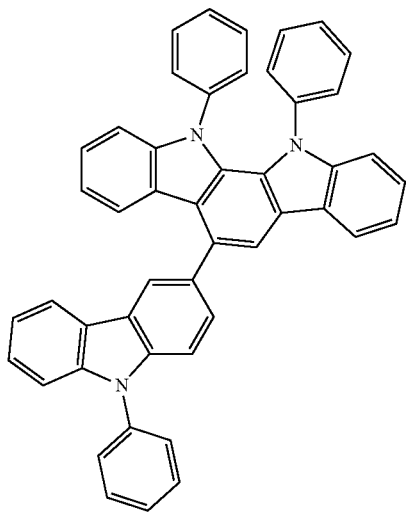

HOST-2

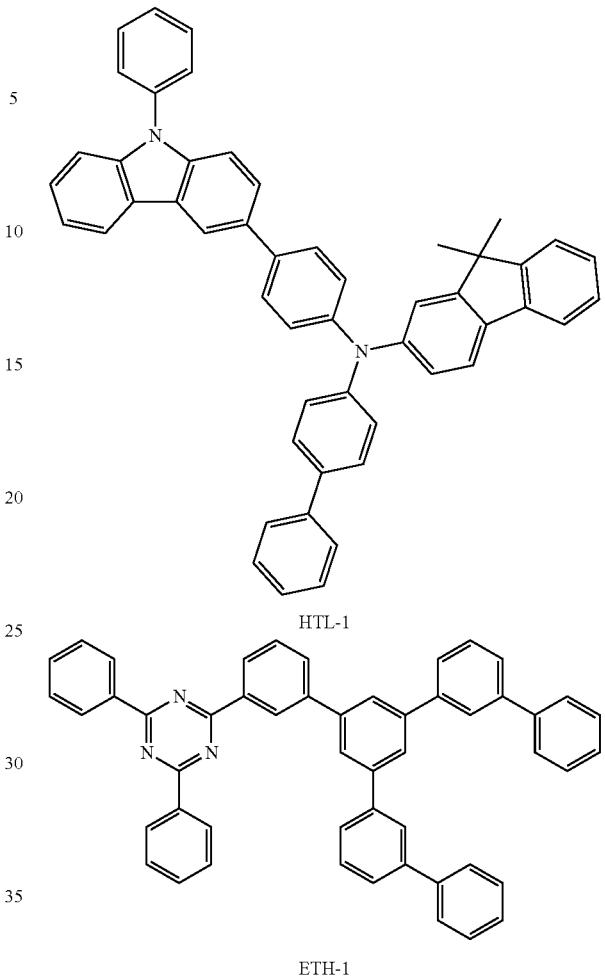

HTL-1

ETH-1

Manufacture of Organic Light Emitting Diode

EXAMPLE 1

A glass substrate disposed with ITO electrode was cut into a size of 50 mm×50 mm×0.5 mm and then, ultrasonic wave cleaned with acetone isopropyl alcohol and pure water respectively for 15 minutes and UV ozone cleaned for 30 minutes.

On the ITO electrode, m-MTDATA was vacuum-deposited at 1 Å/sec to form a 600 Å-thick hole injection layer, and on the hole injection layer, Compound HTL-1 was vacuum-deposited at 1 Å/sec to form a 300 Å thick hole transport layer. Subsequently, on the hole transport layer, Ir(ppy)$_3$ (a dopant), Compound A-5 according to Synthesis Example 1, and Compound ETH-1 were codeposited in a weight ratio of 10:45:45 to form a 400 Å-thick light emitting layer. On the light emitting layer, BAlq was vacuum-deposited at 1 Å/sec to form a 50 Å-thick hole blocking layer, and on the hole blocking layer, Alq$_3$ was vacuum-deposited to form a 300 Å-thick electron transport layer. On the electron transport layer, LiF 10 Å (an electron injection layer (EIL)) and Al 2000 Å (a cathode) were sequentially vacuum-deposited to manufacture an organic light emitting diode.

EXAMPLES 2 to 7

Each organic light emitting diode according to Examples 2 to 7 was manufactured according to the same method as Example 1 except for respectively using Compound A-6, Compound C-5, Compound D-5, Compound D-7, Compound F-2, and Compound F-5 according to Synthesis Examples 2 to 7 instead of Compound A-1 according to Synthesis Example 1.

COMPARATIVE EXAMPLE 1

An organic light emitting diode according to Comparative Synthesis Example 1 was manufactured according to the same method as Example 1 except for using Host-1 according to Comparative Synthesis Example 1 instead of Compound A-1 according to Synthesis Example 1.

COMPARATIVE EXAMPLE 2

An organic light emitting diode according to Comparative Synthesis Example 2 was manufactured according to the same method as Example 1 except for using Host-2 according to Comparative Synthesis Example 2 instead of Compound A-1 according to Synthesis Example 1.

Performance Measurement of Organic Light Emitting Diode

Driving voltages, luminous efficiency, and life-span characteristics of organic light emitting diodes according to Examples 1 to 7 and Comparative Examples 1 and 2 were measured. The measurement methods are as follows.

1) Measurement of Current Density Change Depending on Voltage Change

Current values flowing in the unit device of the manufactured organic light emitting diodes according to Examples 1 to 7 and Comparative Examples 1 and 2 were measured for, while increasing the voltage using a current-voltage meter (Keithley 2400), and the measured current values were divided by an area to provide the results.

2) Measurement of Luminance Change Depending on Voltage Change

Luminance of the manufactured organic light emitting diodes according to Examples 1 to 7 and Comparative Examples 1 and 2 was measured for luminance, while increasing the voltage using a luminance meter (Minolta Cs-1000A).

3) Measurement of Luminous Efficiency

Luminous efficiency was calculated by using the luminance, current density, and voltages (V) from "1) Measurement of Current Density Change Depending on Voltage Change" and "2) Measurement of Luminance Change Depending on Voltage Change", and the results are shown in Table 1.

TABLE 1

| Nos. | Host of light emitting layer | Driving voltage (V) | Luminous efficiency (cd/A) | Life-spanT97(h) |
|---|---|---|---|---|
| Example 1 | A-5 | 3.89 | 112.3 | *** |
| Example 2 | A-6 | 3.61 | 106.9 | 157 |
| Example 3 | C-5 | 3.46 | 107.4 | *** |
| Example 4 | D-5 | 3.75 | 110.4 | 200 |
| Example 5 | D-7 | 3.62 | 109.3 | 197 |
| Example 6 | F-2 | 3.36 | 111.2 | 250 |
| Example 7 | F-5 | 3.59 | 110.4 | 245 |
| Comparative Example 1 | Host 1 | 4.24 | 84.6 | 155 |
| Comparative Example 2 | Host 2 | 4.15 | 91.4 | 60 |

***not measured

Referring to Table 1, the organic light emitting diodes according to Examples 1 to 7 showed a remarkably low driving voltage and at least greater than or equal to 16% improved luminous efficiency compared with the organic light emitting diodes according to Comparative Examples 1 and 2. In addition, comparing measured life-span data, the organic light emitting diodes according to Examples showed a little improved life-span compared with the organic light emitting diodes according to Comparative Examples.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

200, 300: organic light emitting diode
105: organic layer
110: anode
120: cathode
130: light emitting layer
140: hole auxiliary layer
141: hole transport layer
142: hole transport auxiliary layer

The invention claimed is:

1. An organic compound having a structure in which moieties represented by Chemical Formulae 1 to 3 are bonded in order:

[Chemical Formula 1]

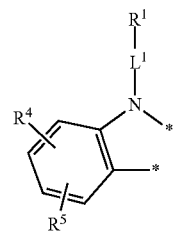

[Chemical Formula 2]

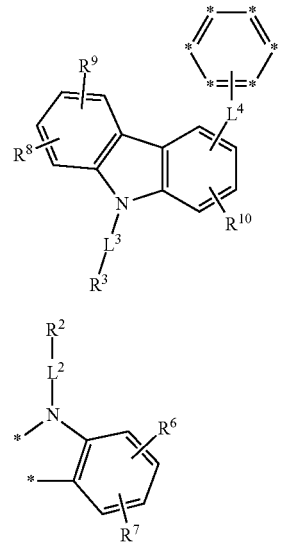

[Chemical Formula 3]

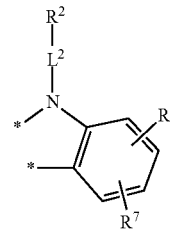

wherein, in Chemical Formulae 1 to 3, adjacent two *'s of Chemical Formula 2 are bonded with two *'s of Chemical Formula 1, other adjacent two *'s of Chemical Formula 2 are bonded with two *'s of Chemical Formula 3,

* not being bonded with Chemical Formula 1 or 3 is C or $CR^{11}$, $L^1$ to $L^3$ are independently a single bond or a substituted or unsubstituted C6 to C20 arylene group, $L^4$ is a substituted or unsubstituted C6 to C20 arylene group, $R^1$ to $R^{10}$ are independently hydrogen, deuterium, a substituted or unsubstituted C1 to C20 alkyl group, a substituted or unsubstituted C6 to C30 aryl group, a substituted or unsubstituted amino group, or a combination thereof, and $R^{11}$ is hydrogen, deuterium, a C1 to C20 alkyl group, a C6 to C12 aryl group, a substituted or unsubstituted amino group, or a combination thereof, provided, that the moieties represented by Chemical Formulae 1 to 3 do not have the following structure,

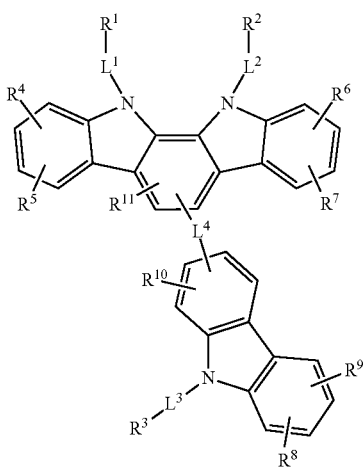

wherein, $L^1$ to $L^4$, and $R^1$ to $R^{11}$ are the same as defined above.

2. The organic compound of claim 1, wherein $L^4$ is a substituted or unsubstituted phenylene group, a substituted or unsubstituted naphthylene group, a substituted or unsubstituted biphenylene group, a substituted or unsubstituted terphenylene group, or a combination thereof.

3. The organic compound of claim 1, wherein $L^4$ is a substituted or unsubstituted m-phenylene group, a substituted or unsubstituted p-phenylene group, or a combination thereof.

4. The organic compound of claim 1, wherein $R^1$ to $R^3$ are independently a substituted or unsubstituted phenyl group, a substituted or unsubstituted biphenyl group, or a substituted or unsubstituted terphenyl group.

5. The organic compound of claim 1, wherein the organic compound is represented by one of Chemical Formulae 4 to 7:

[Chemical Formula 4]

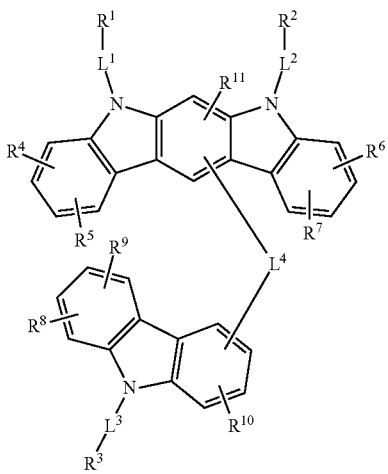

[Chemical Formula 5]

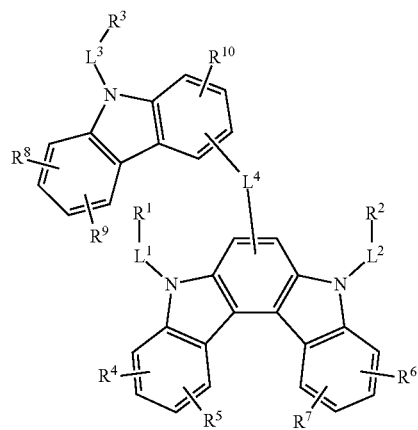

[Chemical Formula 6]

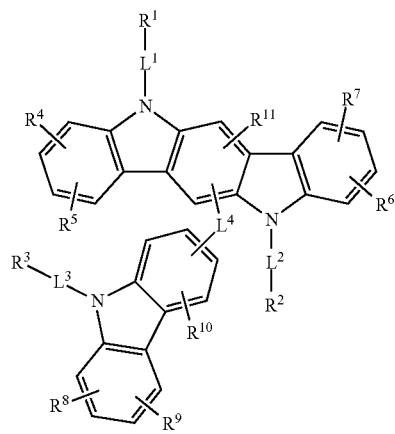

[Chemical Formula 7]

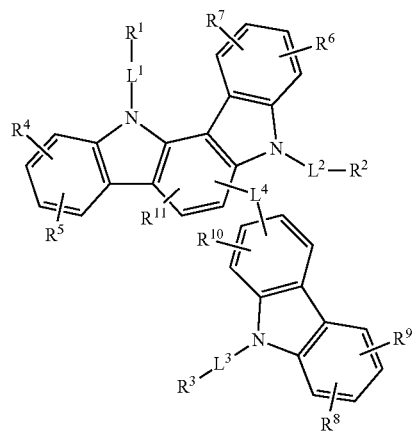

wherein, in Chemical Formulae 4 to 7, $L^1$ to $L^3$ are independently a single bond or a substituted or unsubstituted C6 to C20 arylene group, $L^4$ is a substituted or unsubstituted C6 to C20 arylene group, $R^1$ to $R^{10}$ are independently hydrogen, deuterium, a substituted or unsubstituted C1 to C20 alkyl group, a substituted or unsubstituted C6 to C30 aryl group, a substituted or unsubstituted amino group, or a combination thereof, and R[11] is hydrogen, deuterium, a C1 to C20 alkyl group, an unsubstituted C6 to C12 aryl group, a substituted or unsubstituted amino group, or a combination thereof.

6. The organic compound of claim 5, wherein the organic compound is represented by Chemical Formula 4 and the organic compound represented by Chemical Formula 4 is represented by one of Chemical Formulae 4a to 4d:

[Chemical Formula 4a]

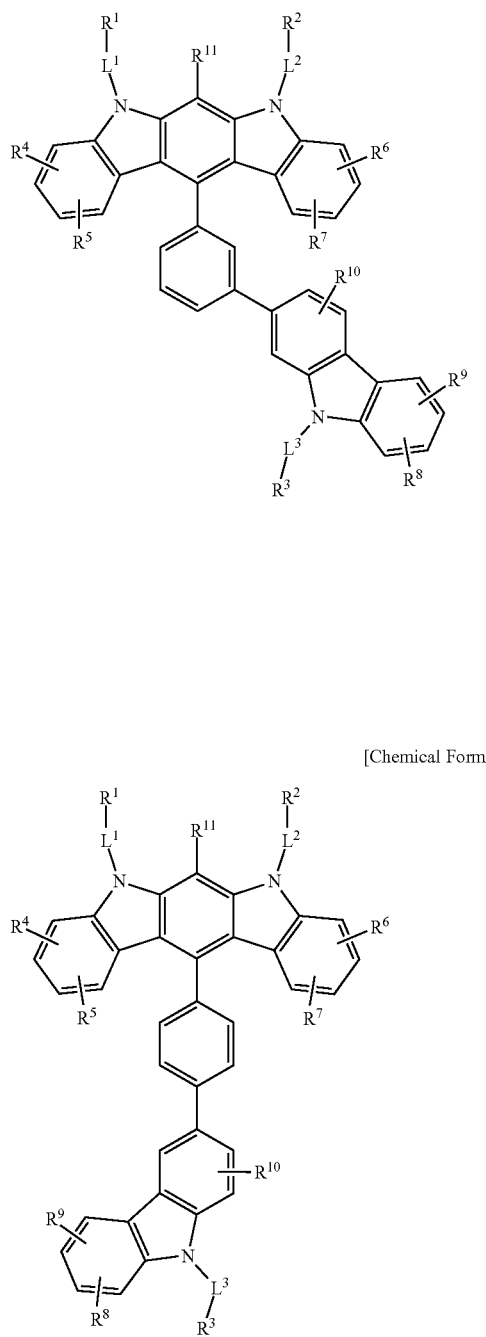

[Chemical Formula 4b]

[Chemical Formula 4c]

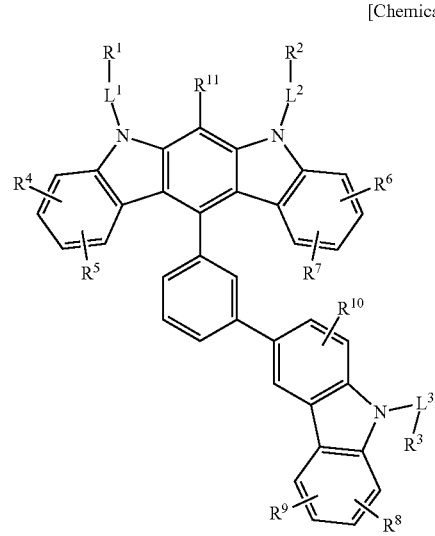

[Chemical Formula 4d]

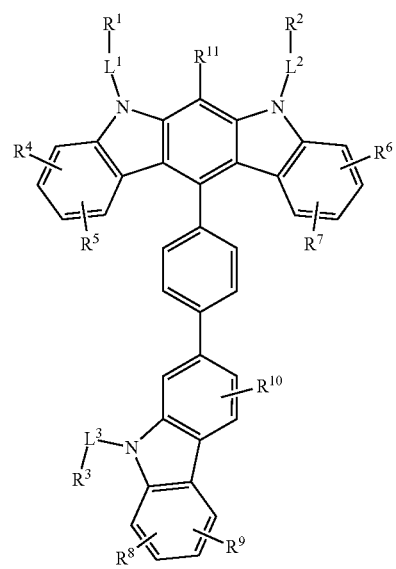

wherein, in Chemical Formulae 4a to 4d, $L^1$ to $L^3$ are independently a single bond or a substituted or unsubstituted C6 to C20 arylene group, $R^1$ to $R^{10}$ are independently hydrogen, deuterium, a substituted or unsubstituted C1 to C20 alkyl group, a substituted or unsubstituted C6 to C30 aryl group, a substituted or unsubstituted amino group, or a combination thereof, and $R^{11}$ is hydrogen, deuterium, a C1 to C20 alkyl group, an unsubstituted C6 to C12 aryl group, a substituted or unsubstituted amino group, or a combination thereof.

7. The organic compound of claim 5, wherein the organic compound is represented by Chemical Formula 5 and the organic compound represented by Chemical Formula 5 is represented by one of Chemical Formulae 5a to 5d:

[Chemical Formula 5a]

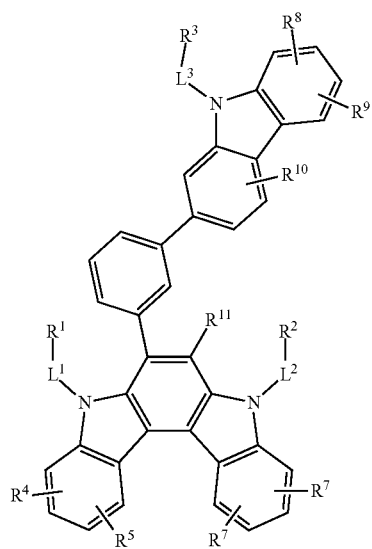

[Chemical Formula 5b]

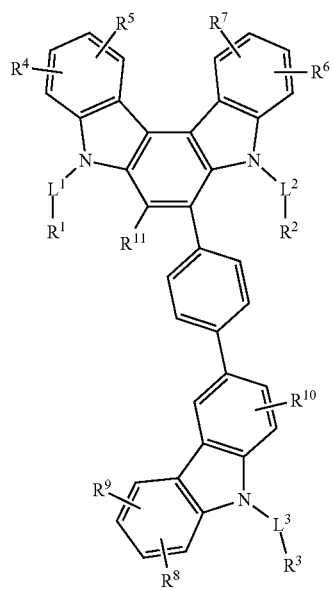

[Chemical Formula 5c]

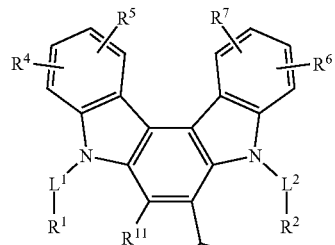

[Chemical Formula 5d]

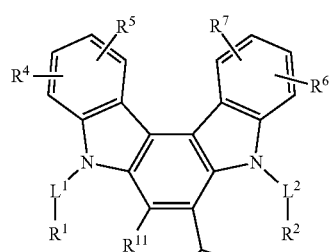

wherein, in Chemical Formulae 5a to 5d, $L^1$ to $L^3$ are independently a single bond or a substituted or unsubstituted C6 to C20 arylene group, $R^1$ to $R^{10}$ are independently hydrogen, deuterium, a substituted or unsubstituted C1 to C20 alkyl group, a substituted or unsubstituted C6 to C30 aryl group, a substituted or unsubstituted amino group, or a combination thereof, and $R^{11}$ is hydrogen, deuterium, a C1 to C20 alkyl group, a C6 to C12 aryl group, a substituted or unsubstituted amino group, or a combination thereof.

8. The organic compound of claim 5, wherein the organic compound is represented by Chemical Formula 6 and the organic compound represented by Chemical Formula 6 is represented by one of Chemical Formulae 6a to 6d:

[Chemical Formula 6a]

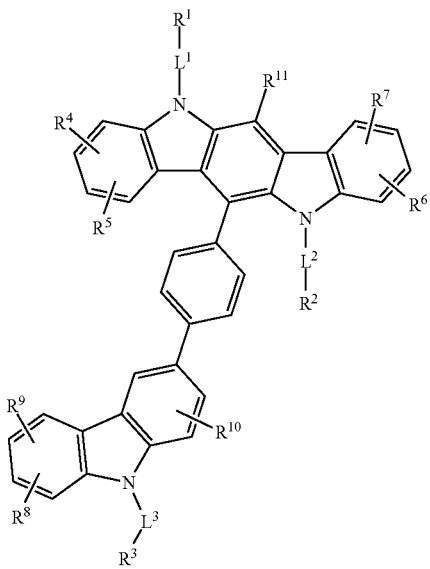

[Chemical Formula 6b]

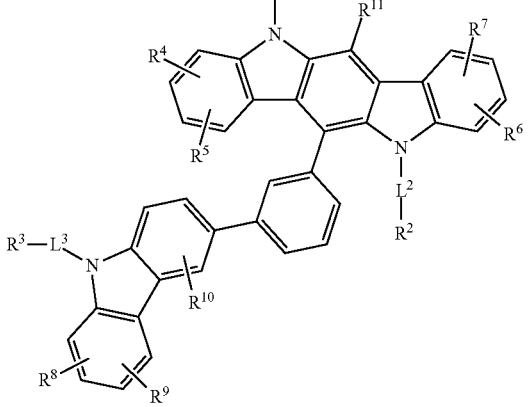

[Chemical Formula 6c]

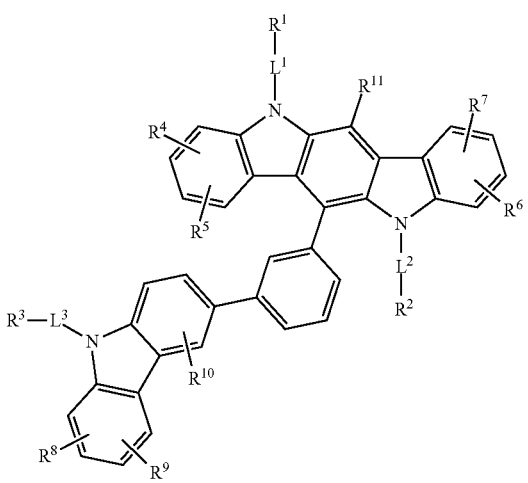

[Chemical Formula 6d]

wherein, in Chemical Formulae 6a to 6d, $L^1$ to $L^3$ are independently a single bond or a substituted or unsubstituted C6 to C20 arylene group, $R^1$ to $R^{10}$ are independently hydrogen, deuterium, a substituted or unsubstituted C1 to C20 alkyl group, a substituted or unsubstituted C6 to C30 aryl group, a substituted or unsubstituted amino group, or a combination thereof, and $R^{11}$ is hydrogen, deuterium, a C1 to C20 alkyl group, a C6 to C12 aryl group, a substituted or unsubstituted amino group, or a combination thereof.

9. The organic compound of claim 5, wherein the organic compound is represented by Chemical Formula 7 and the organic compound represented by Chemical Formula 7 is represented by one of Chemical Formulae 7a to 7h:

[Chemical Formula 7a]

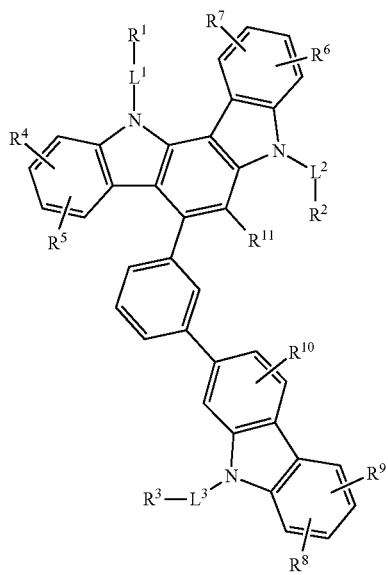

[Chemical Formula 7b]
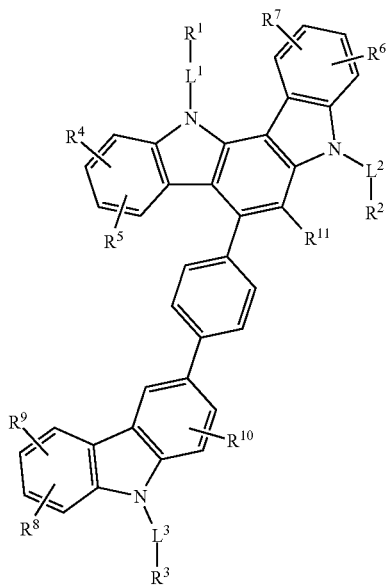
[Chemical Formula 7c]
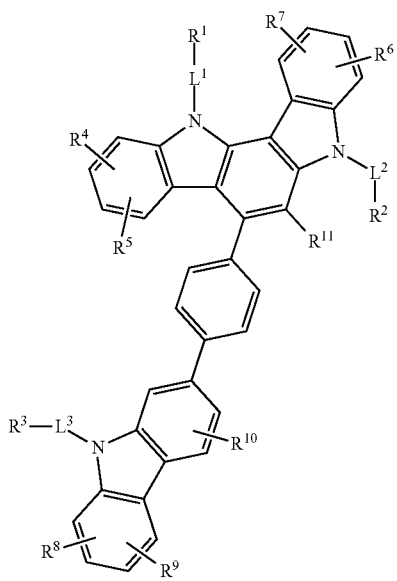
[Chemical Formula 7d]
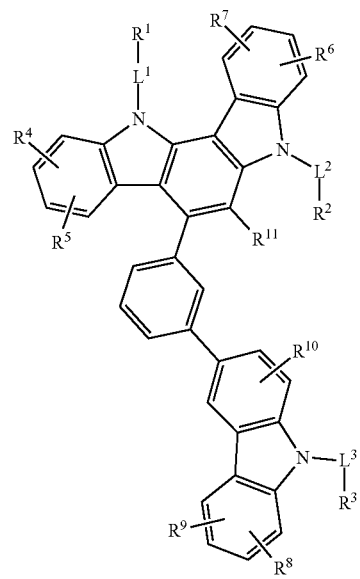
[Chemical Formula 7e]
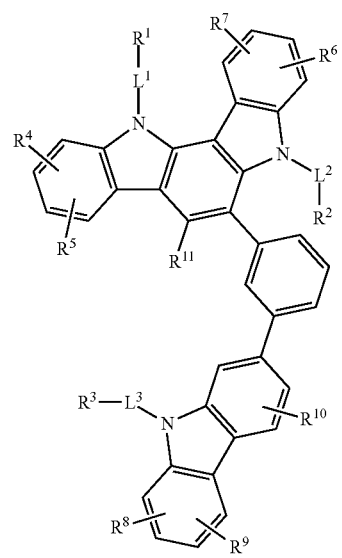

-continued

[Chemical Formula 7f]

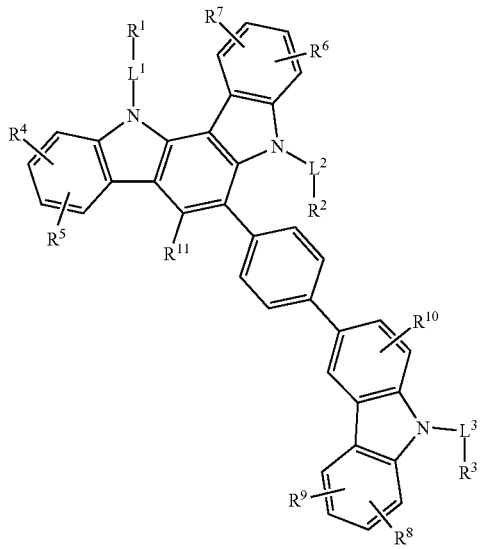

[Chemical Formula 7g]

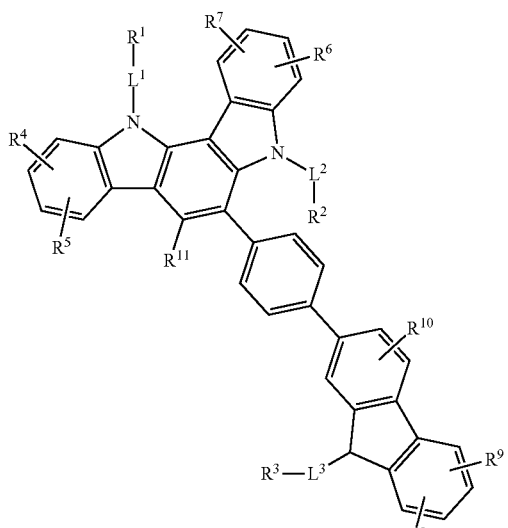

[Chemical Formula 7h]

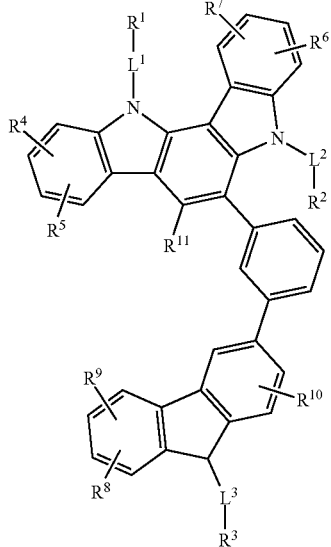

wherein, in Chemical Formulae 7a to 7h, $L^1$ to $L^3$ are independently a single bond or a substituted or unsubstituted C6 to C20 arylene group, $R^1$ to $R^{10}$ are independently hydrogen, deuterium, a substituted or unsubstituted C1 to C20 alkyl group, a substituted or unsubstituted C6 to C30 aryl group, a substituted or unsubstituted amino group, or a combination thereof, and $R^{11}$ is hydrogen, deuterium, a C1 to C20 alkyl group, a C6 to C12 aryl group, a substituted or unsubstituted amino group, or a combination thereof.

10. The organic compound of claim 1, wherein the organic compound is one selected from the compounds listed in Group 1:

[Group 1]

[A-1]

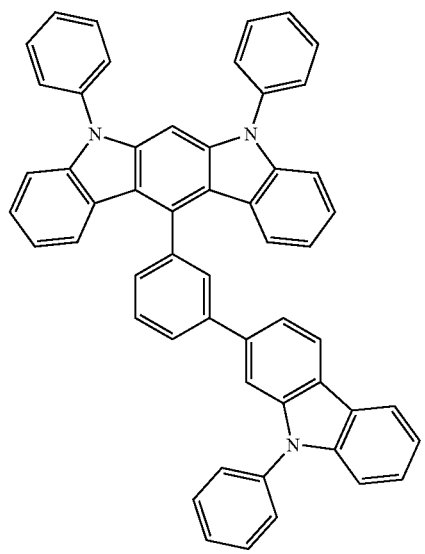

[A-2]

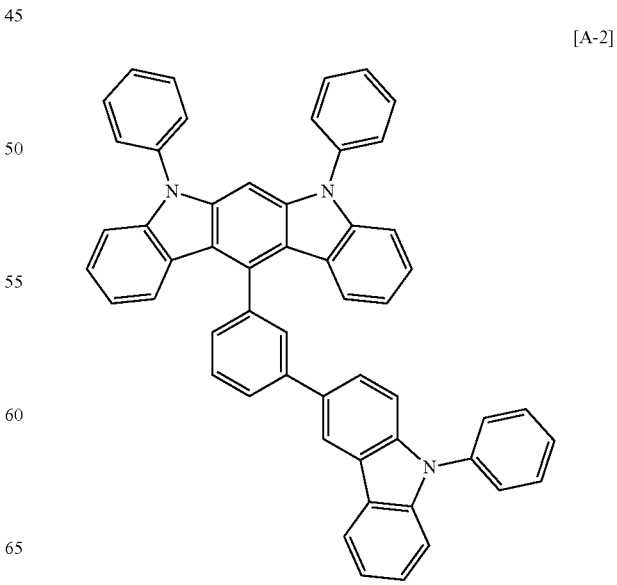

[A-3]
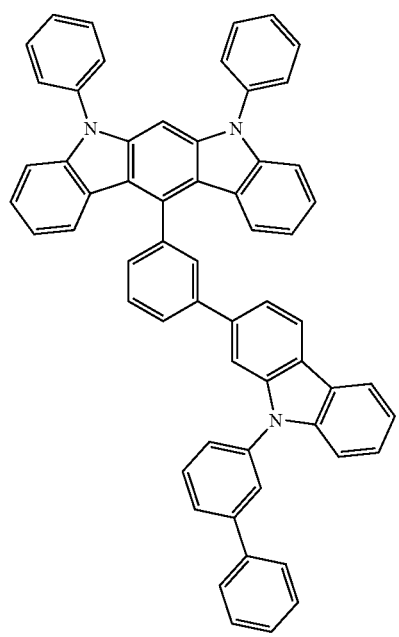
[A-4]
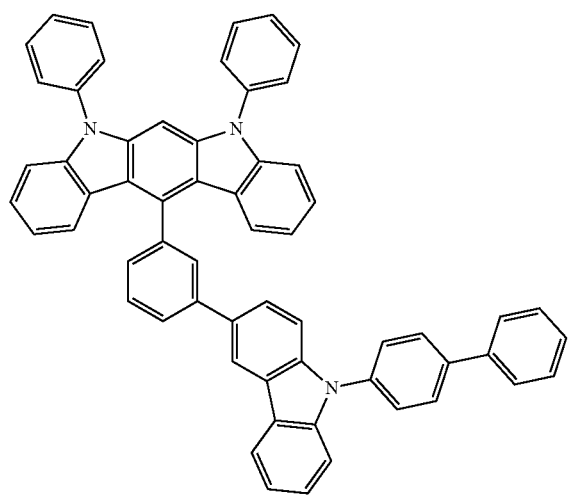
[A-5]
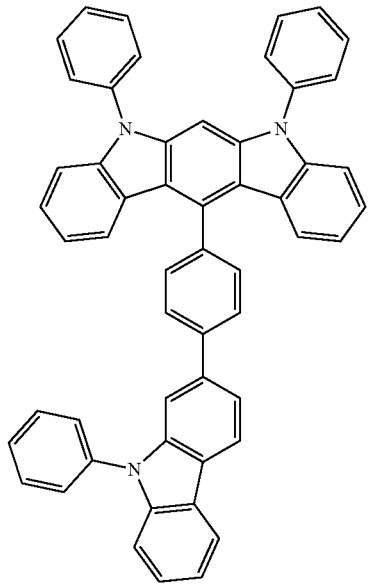
[A-6]
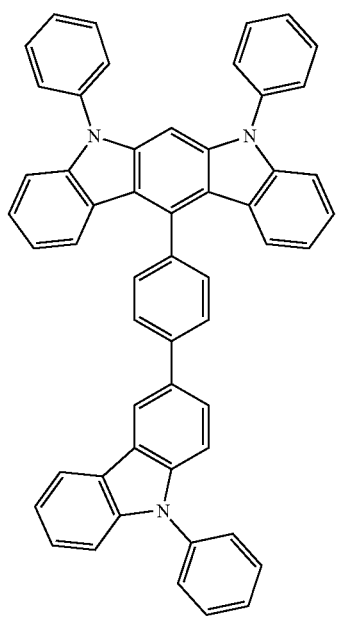

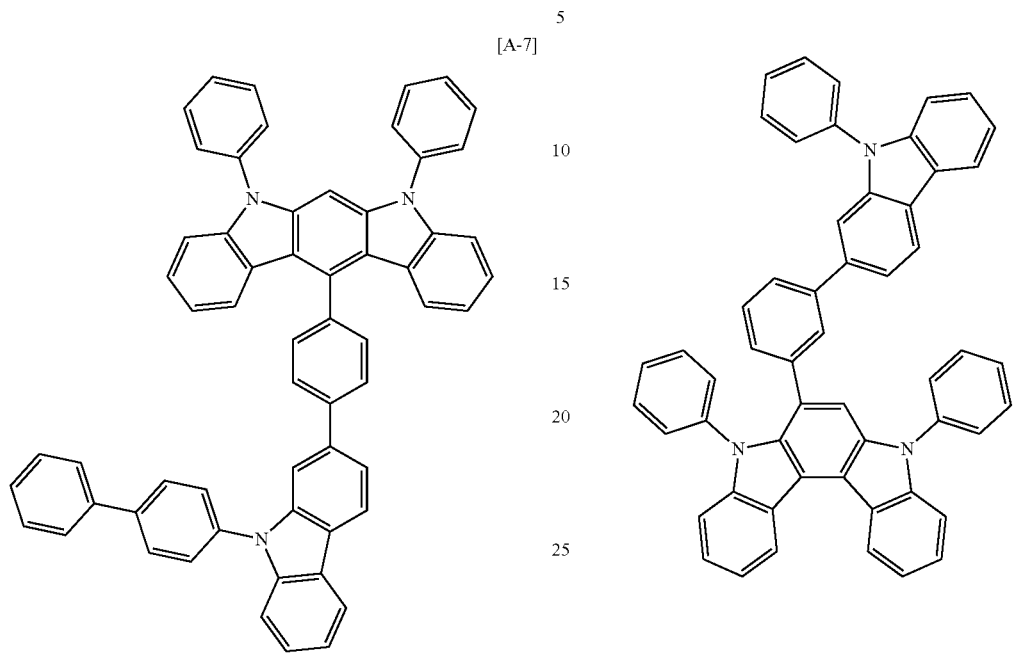
[A-7]
[C-1]
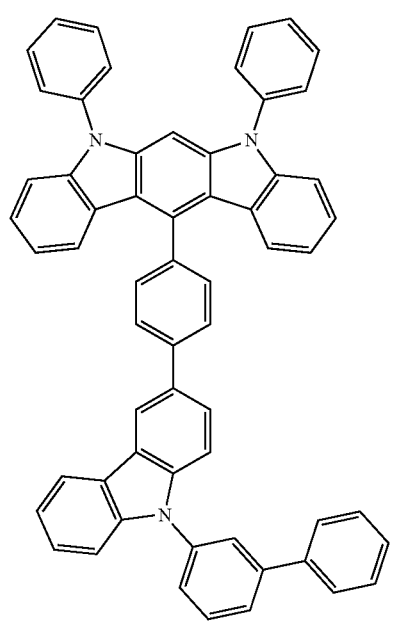
[A-8]
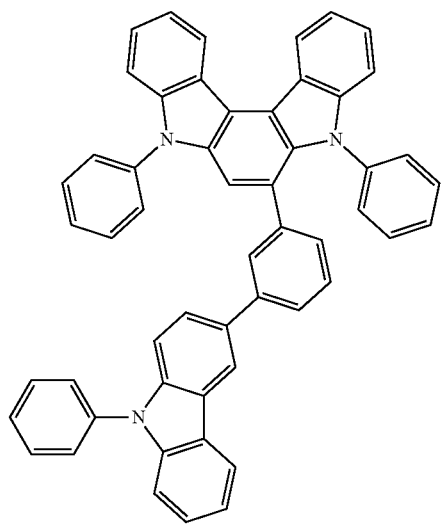
[C-2]

[C-3]
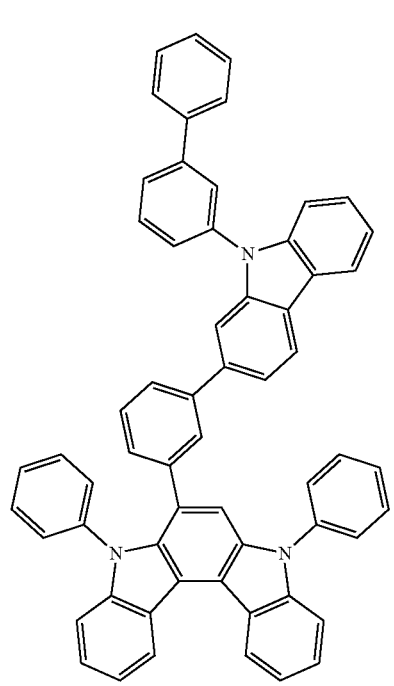
[C-4]
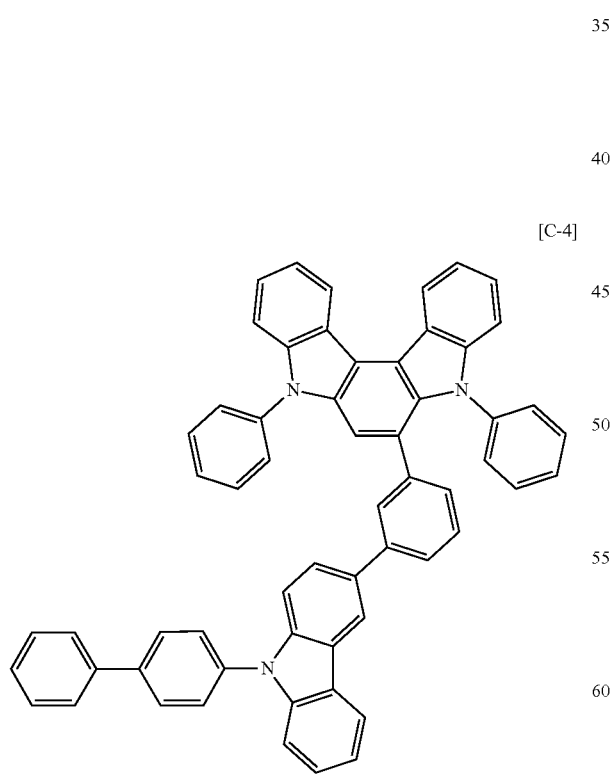
[C-5]
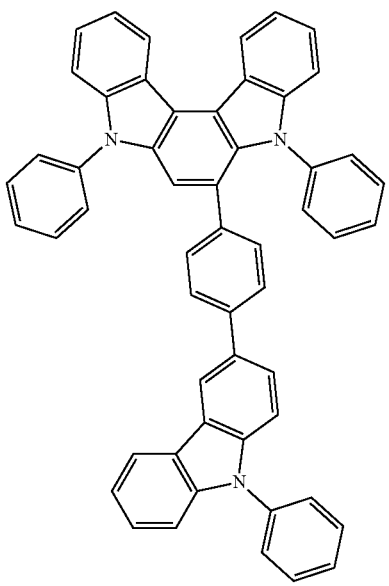
[C-6]
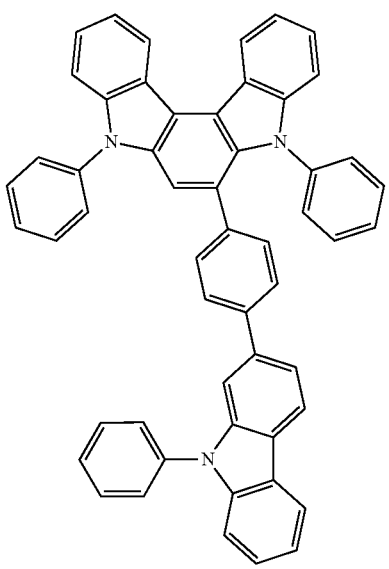

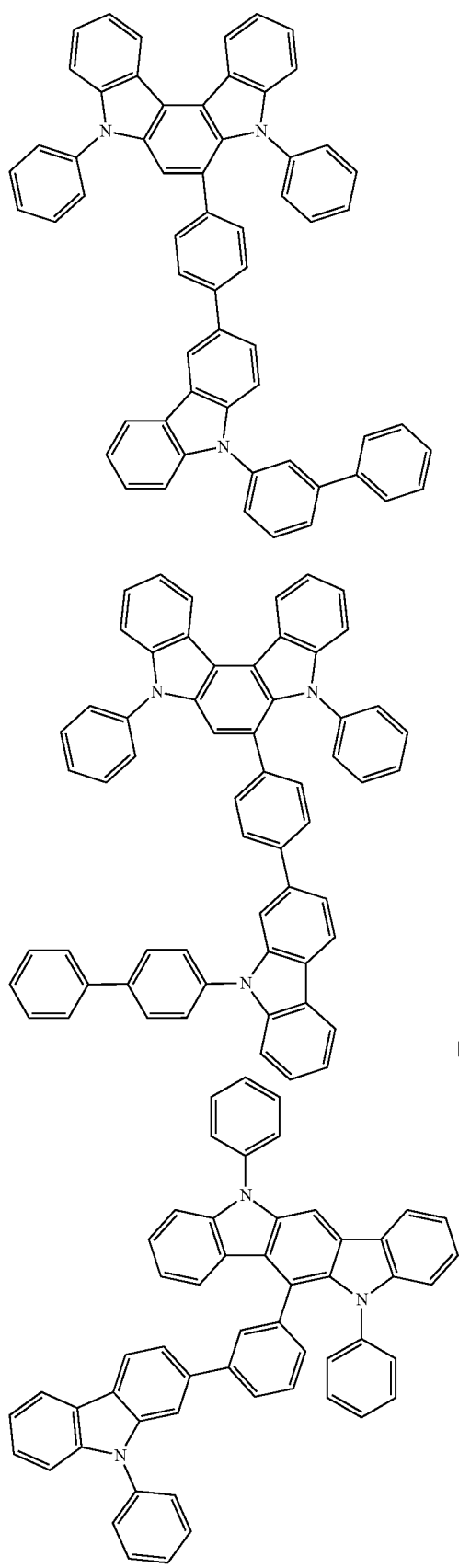
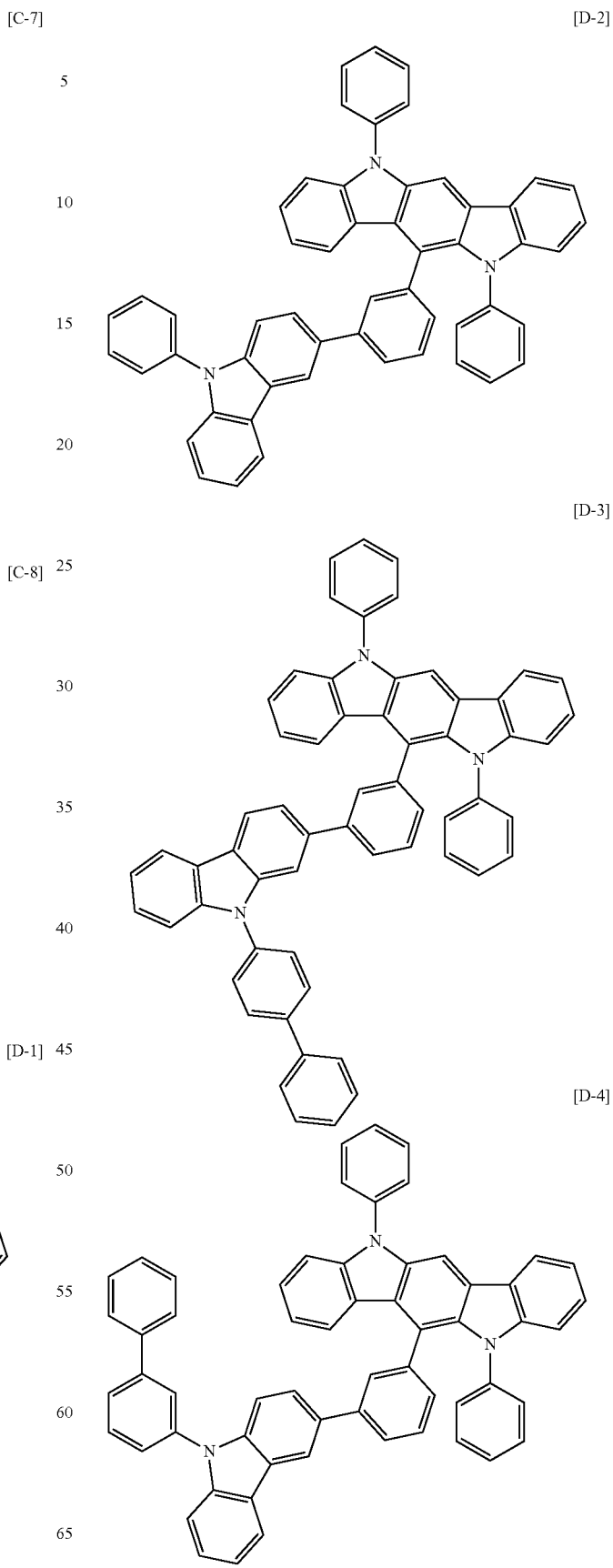

[D-5]
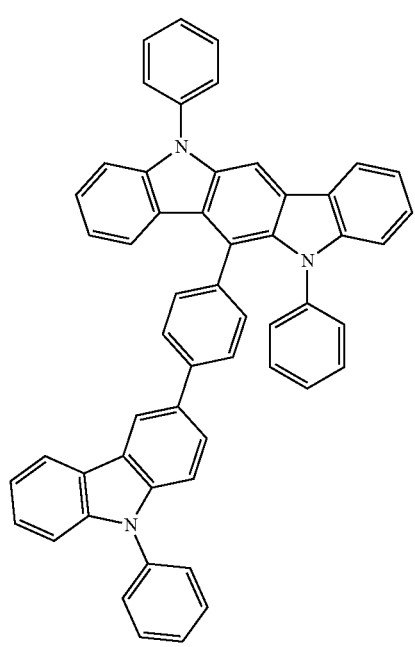
[D-6]
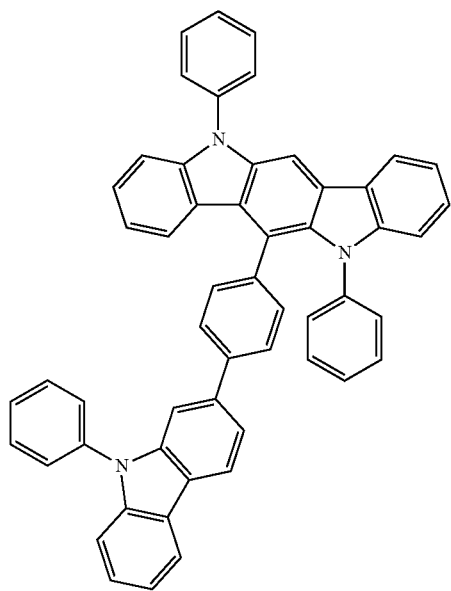
[D-7]
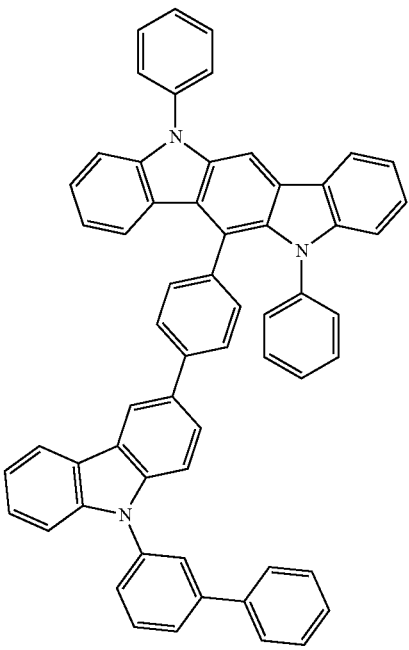
[D-8]
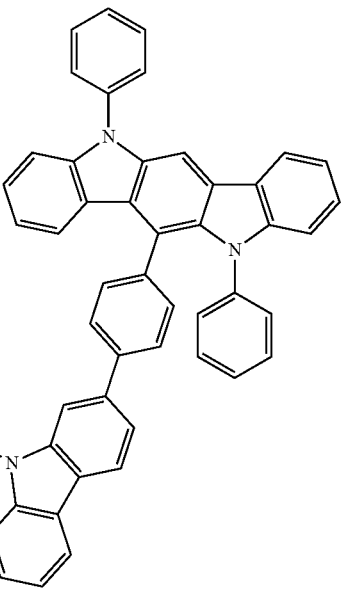

[E-1]
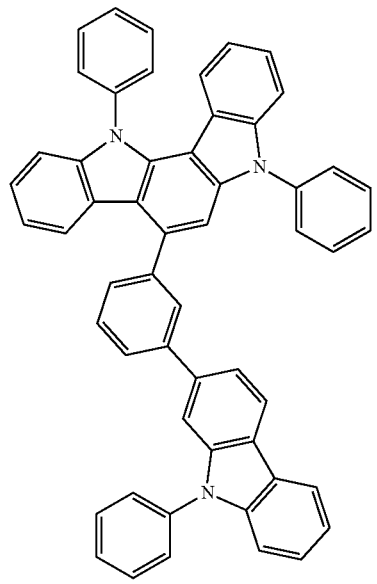
[E-2]
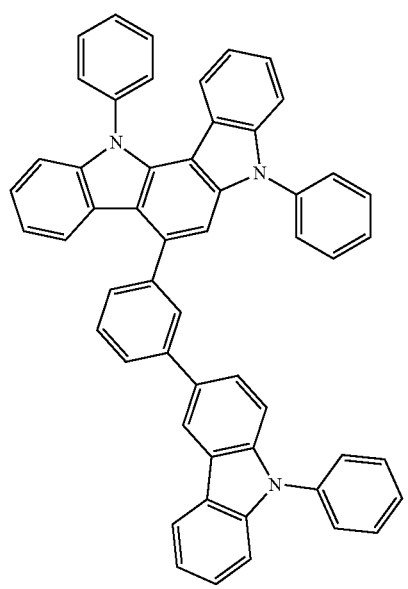
[E-3]
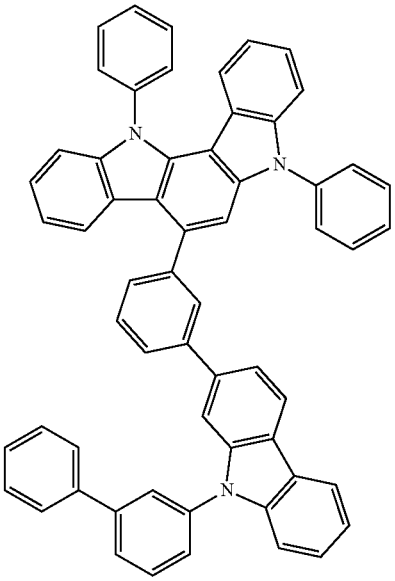
[E-4]
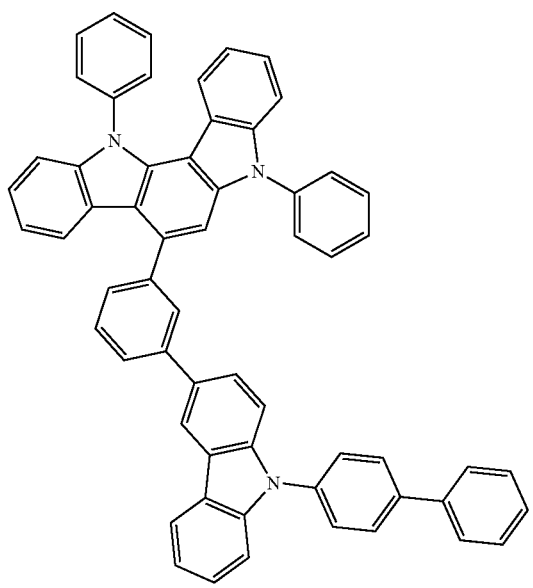

[E-5]
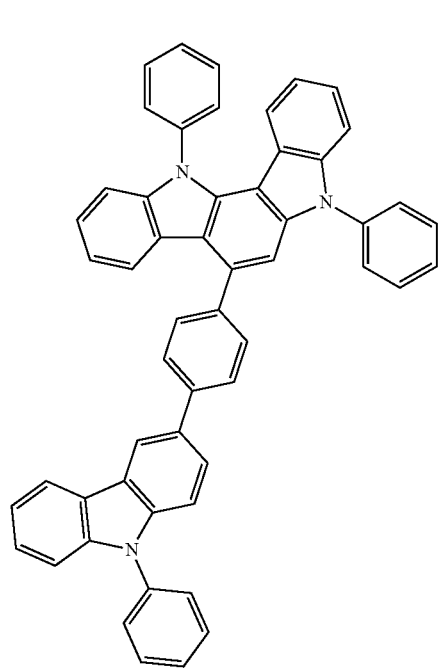
[E-7]
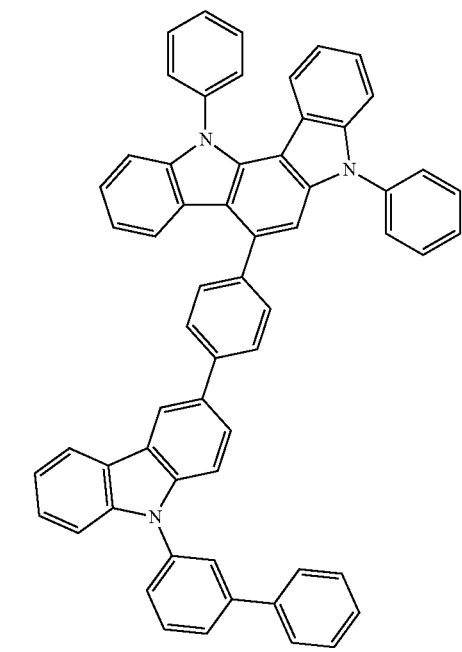
[E-6]
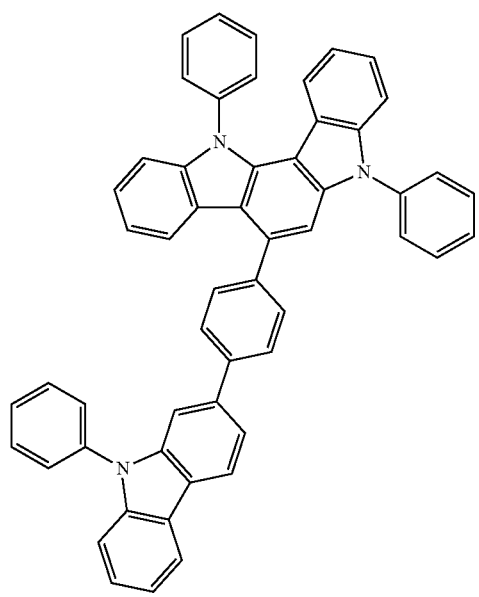
[E-8]
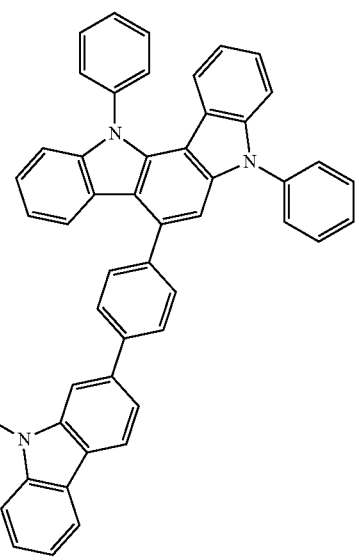

-continued
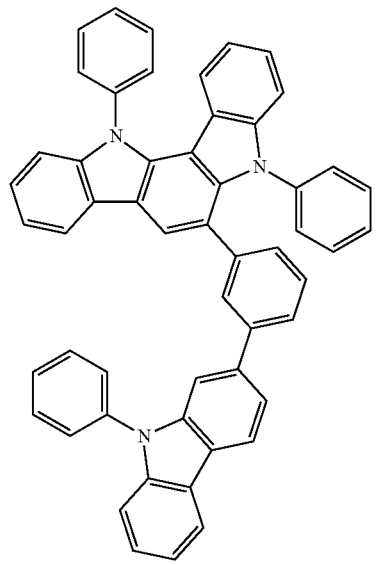
[F-1]
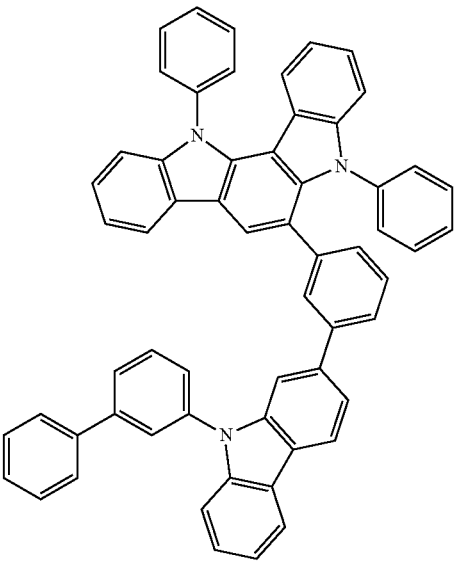
[F-3]
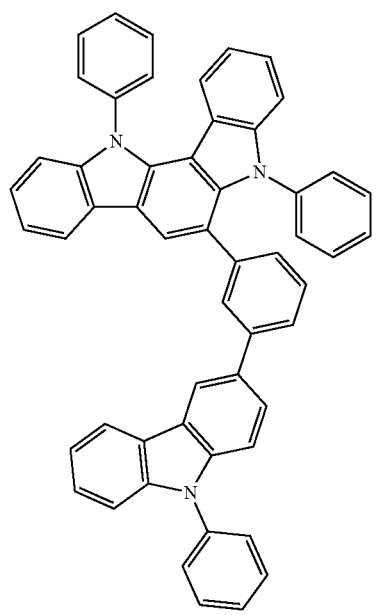
[F-2]
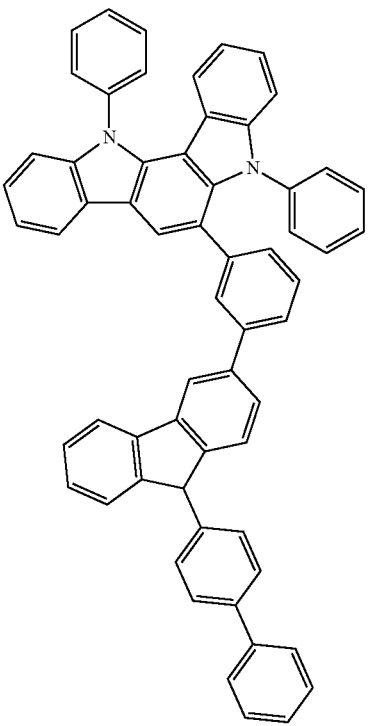
[F-4]

-continued

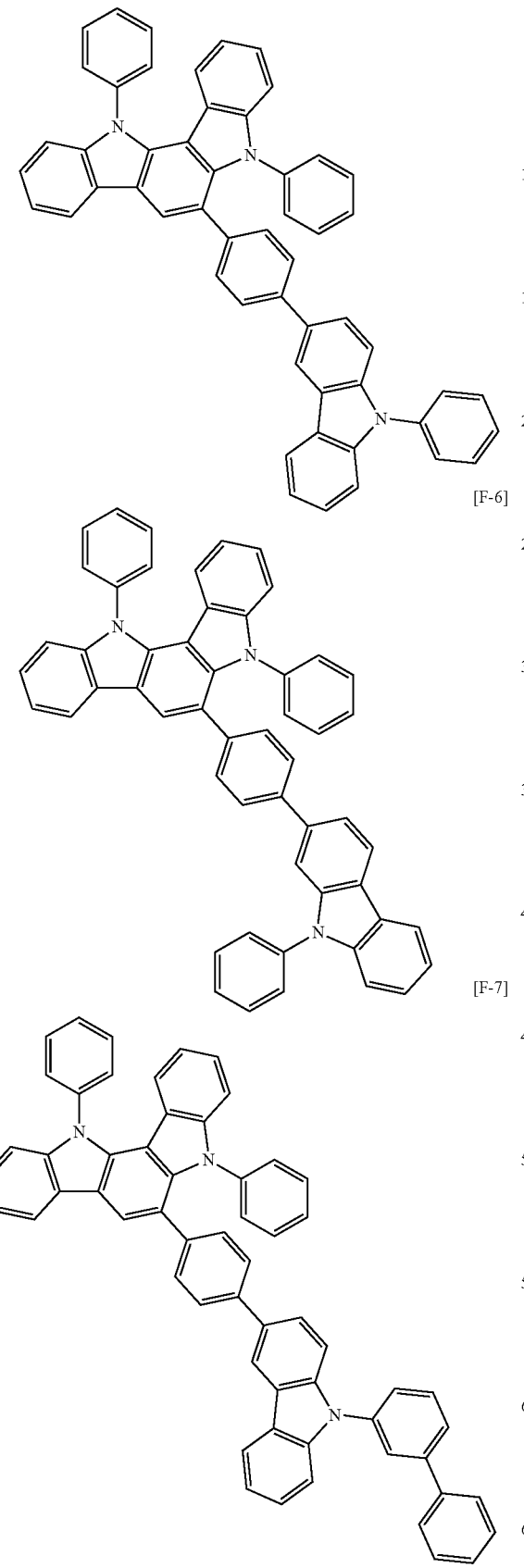

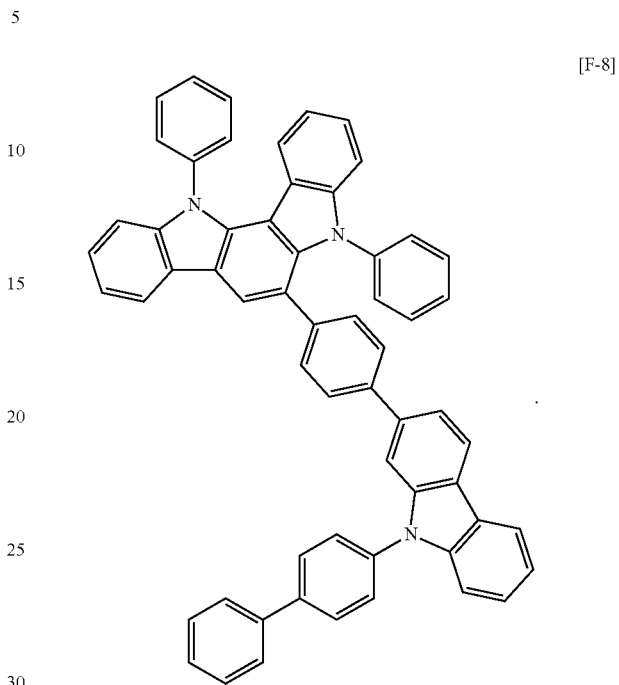

11. An organic optoelectronic device, comprising
   an anode and a cathode facing each other, and
   at least one organic layer disposed between the anode and the cathode
   wherein the organic layer includes the organic compound of claim 1.

12. The organic optoelectronic device of claim 11, wherein the organic layer comprises a light emitting layer comprising the organic compound.

13. The organic optoelectronic device of claim 12, wherein the light emitting layer comprises the organic compound as a first host, and, as a second host, a compound comprising a substituted or unsubstituted triazinyl group, or a substituted or unsubstituted pyrimidinyl group.

14. The organic optoelectronic device of claim 13, wherein the second host is a compound including a triazinyl group substituted with a C6 to C60 aryl group or a compound including a pyrimidinyl group substituted with a C6 to C60 aryl group.

15. A display apparatus comprising the organic optoelectronic device of claim 11.

* * * * *